(12) United States Patent
Deiters

(10) Patent No.: US 8,247,540 B2
(45) Date of Patent: Aug. 21, 2012

(54) CAGED NUCLEOTIDES AND OLIGONUCLEOTIDES AND THEIR APPLICATION

(76) Inventor: Alexander Deiters, Raleigh, NC (US)

( * ) Notice: Subject to any disclaimer, the term of this patent is extended or adjusted under 35 U.S.C. 154(b) by 355 days.

(21) Appl. No.: 12/329,468

(22) Filed: Dec. 5, 2008

(65) Prior Publication Data

US 2010/0099159 A1 Apr. 22, 2010

(51) Int. Cl.
*C07G 3/00* (2006.01)
*C07H 21/02* (2006.01)
*C07H 21/00* (2006.01)
*C07H 19/04* (2006.01)
*C12Q 1/68* (2006.01)

(52) U.S. Cl. ...... 536/4.1; 536/23.1; 536/25.3; 536/26.6; 435/6

(58) Field of Classification Search ............... 536/4.1, 536/23.1, 25.3, 26.6; 435/6
See application file for complete search history.

(56) References Cited

OTHER PUBLICATIONS

Ando et al., Nature Genetics, 28:317-325, 2001.
Bayer and Smolke, Nature Biotechnology 23:337-343, 2005.
Breaker-1, Curr. Opinion Biotechnology 13:31-39, 2002.
Breaker-2, Nature, 432:838-845, 2004.
Dorman and Prestwick, Tibtech, 18:64-77, 2000.
Doudna and Cech, Nature 418:222-228, 2002.
Fire et al., Nature 391:806-811, 1998.
Heckel and Mayer, J. Am. Chem. Soc. 127:822-823, 2005.
Keiper and Vyle, Angew Chemie 45:3306-3309, 2006.
Krock and Heckel Angew Chemie, 44:471-473, 2005.
Lawrence, Curr. Op. Chemical Biol. 9:570-575, 2005.
Liu and Sen, J. Mol. Biol. 341:887-892, 2004.
Mandal and Breaker, Nature Reviews, 5:451-463, 2004.
Mayer and Heckel, Angew. Chemie, 45:4900-4921, 2006.
Santoro and Joyce, Proc. Natl. Acad. Sci. USA 94:4264-4266, 1997.
Scherer and Rossi, Nature Biotechnology 21:1457-1465, 2003.
Shah et al., Agnew. Chemie 44:1328-1332, 2005.
Tang and Dmochowski-1 Mol. BioSyst. 3:100-110, 2007.
Ting et al. J. Am. Chem. Soc. 126:12720-12731, 2004.
Young and Deiters Org. Biomol. Chem. 5:999-1005, 2007.
Lusic et al. Org. Lett. 9:1903-1906, 2007.
Mikat and Heckel RNA 13:2341-2347, 2007.
Hobartner and Silverman Angew. Chemie 44:7305-7309, 2005.
Lusic and Deiters Synthesis 13:2147-2150, 2006.
Tang and Dmochowski-2 Org. Lett. 7:279-282, 2005.

*Primary Examiner* — Jezia Riley
(74) *Attorney, Agent, or Firm* — Jeffrey Oster

(57) ABSTRACT

There is disclosed nucleotides and nucleotide analogs having a protecting or "caging" group. There is further disclosed oligonucleotides and oligonucleotides analogs formed having a protecting or "caging" group. There is further disclosed a method for decaging the nucleotides and nucleotide analogs having a protecting or "caging" group and oligonucleotides and oligonucleotide analogs having a caging group.

15 Claims, 3 Drawing Sheets

CAGED NUCLEOTIDES AND OLIGONUCLEOTIDES AND THEIR APPLICATION

TECHNICAL FIELD

The present disclosure provides nucleotides and nucleotide analogs having a protecting or "caging" group thereon. The present disclosure further provides oligonucleotides and oligonucleotides analogs formed having a protecting or "caging" group thereon. The present disclosure further provides a method for decaging nucleotides and nucleotide analogs having a protecting or "caging" group.

BACKGROUND

Discoveries have revealed the multifactorial roles oligonucleotides play in vitro and in vivo. It has been demonstrated, that oligonucleotides can act as catalysts (ribozymes and DNAzymes) (J. Doudna and T. Cech, Nature 2002, 418, 222; S. Santoro and G. Joyce, Proc. Natl. Acad. Sci. U.S.A. 1997, 94, 4262), sensors (aptamers) (R. Breaker, Curr. Opin. Biotechnol. 2002, 13, 31), gene expression platforms (riboswitches and antiswitches) (R. Breaker, Nature 2004, 432, 838; M. Mandal and R. Breaker, Nat. Rev. Mol. Cell. Biol. 2004, 5, 451; T. Bayer and C. Smolke, C. D., Nat. Biotechnol. 2005, 23, 337), and gene regulatory elements (antisense DNA, siRNA, and miRNA) (L. Scherer et al., Nat. Biotechnol. 2003, 21, 1457; A. Fire et al., Nature 1998, 391, 806).

In order to study the function of oligonucleotides in a detailed fashion and to employ oligonucleotides as highly specific biological research tools, precise control over their activity in a spatial and a temporal manner is required. In this context, light represents an ideal control element since it can be precisely controlled in amplitude, location, and timing thus imposing spatio-temporal control on the system under study (D. Young and A. Deiters, Org. Biomol. Chem. 2007, 5, 999; X. Tang and I. Dmochowski, Mol. BioSyst. 2007, 3, 100; M. Goeldner and R. Givens, Dynamic Studies in Biology: Phototriggers, Photoswitches and Caged Biomolecules. Wiley-VCH: Weinheim, 2005; p xxvii; G. Mayer and A. Heckel, Angew. Chem. Int. Ed 2006, 45, 4900; G. Dorman and G. Prestwich, Trends Biotechnol. 2000, 18, 64; D. Lawrence, Curr. Opin. Chem. Biol. 2005, 9, 570). The most common technique of conveying light-regulation to biological processes involves the installation of a photo-protecting group on a biologically active molecule which can be completely removed via light irradiation. This process, termed 'caging', has been successfully employed to the light-controlled activation of small molecule inducers of gene expression, fluorophores, peptides, and proteins (Id). DNA and RNA have been caged as well, mostly through statistical reaction of the phosphate backbone of the synthesized or transcribed oligonucleotide with reactive diazo-derivatives of caging groups (S. Shah et al., Angew. Chem. Int. Ed. Engl. 2005, 44, 1328; H. Ando et al., Nat. Genet. 2001, 28, 317). The major disadvantage of this approach is that no control over the position and number of installed caging groups can be achieved. Moreover, caging groups are only installed on the phosphate backbone, not on the heterocyclic base itself, failing to disrupt Watson-Crick base pairing. Recently, approaches to the site-specific caging of DNA have been reported. The introduction of an 0-4 caged thymidine has been successfully applied to the photochemical activation of transcription and aptamer binding (L. Krock and A. Heckel, Angew. Chem. Int. Ed. 2005, 44, 471; A. Heckel and G. Mayer, J. Am. Chem. Soc. 2005, 127, 822). However, due to the lability of the caging group special DNA synthesis conditions were necessary. An adenosine modified with a sterically demanding, photo-removable imidazolylethylthio group has been used to photochemically activate an 8-17E DNAzyme (R. Ting et al., J. Am. Chem. Soc. 2004, 126, 12720). After irradiation for 8-10 min with short-wavelength UV light (254-310 nm) only 30% of RNA cleavage was observed after a 60 min reaction time. Since the caging group was installed at C-8, no hydrogen bonding of the adenosine was disrupted. Reversible switching of DNAzyme activity was previously achieved through incorporation of diazobenzene motifs, however, only a 5- to 9-fold rate modulation upon irradiation was obtained (Y. Liu and D. Sen. J. Mol. Biol. 2004, 341, 887; S. Keiper and J. Vyle, Angew. Chem. Int. Ed. Engl. 2006, 45, 3306).

SUMMARY

The present disclosure provides a caged nucleotide and caged nucleotide analog comprising a caged purine or pyrimidine base selected from the group consisting of:

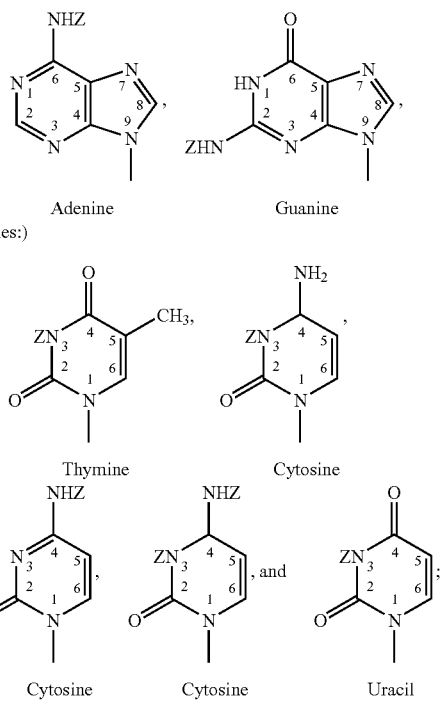

wherein Z is a caging group of the formula:

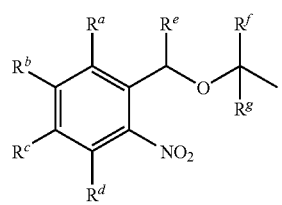

and wherein:

$R^a$, $R^b$, $R^c$ and $R^d$ are each independently selected from the group consisting of H, halo, $C_1$-$C_{20}$ alkyl, $C_1$-$C_{20}$ alkenyl, $C_1$-$C_{20}$ alkynyl, $C_1$-$C_{20}$ alkoxy, aryl, heteroaryl, keto, carboxy, amino, silyl, boron, and targeting groups;

or an adjacent pair of $R^a$ and $R^b$, $R^b$ and $R^c$, or $R^c$ and $R^d$ together form a substituent of the formula —O(CH$_2$)$_n$O—, where n is from 1 to 3; and $R^e$ is selected from the group consisting of H, $C_1$-$C_{20}$ alkyl, $C_1$-$C_{20}$ alkenyl, $C_1$-$C_{20}$ alkynyl, aryl, heteroaryl, keto, carboxy, and targeting groups;

$R^f$ and $R^g$ are each independently selected from the group consisting of consisting of H, $C_1$-$C_{20}$ alkyl, $C_1$-$C_{20}$ alkenyl, $C_1$-$C_{20}$ alkynyl, $C_1$-$C_{20}$ alkoxy, aryl, heteroaryl, keto, carboxy, amino, and targeting groups.

Preferably, at least one of $R^a$, $R^b$, $R^c$ and $R^d$ is $C_1$-$C_{20}$ alkoxy. Preferably, an adjacent pair of $R^a$ and $R^b$, $R^b$ and $R^c$, or $R^c$ and $R^d$ together form a substituent of the formula —O(CH$_2$)$_n$O—, wherein n is an integer from 1 to 3. Preferably, at least one of $R^a$, $R^b$, $R^c$ and $R^d$, $R^e$, $R^f$ and $R^g$ is a targeting group. Preferably, the compound is a phosphoramidite or N,N-dimethylamidophosphorochloridate.

The present disclosure provides a method for synthesizing an oligonucleotide or oligonucleotide analog from a plurality of nucleotides or nucleotide analogs, wherein each of the nucleotides or nucleotide analogs contains a purine or pyrimidine base, wherein at least one of the nucleotides or nucleotide analogs is a caged nucleotide or nucleotide analog selected from the group consisting of:

(Purines:)

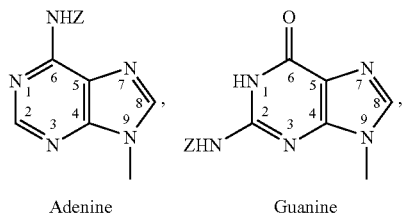

Adenine  Guanine (Pyrimidines:)

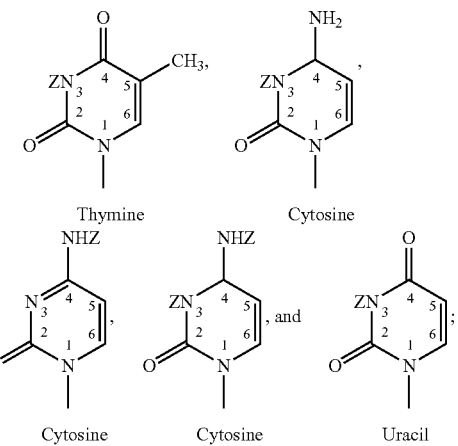

Thymine  Cytosine
Cytosine  Cytosine  Uracil wherein Z is a caging group of the formula:

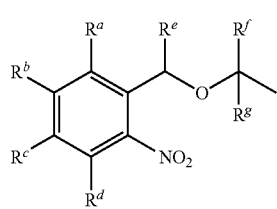

and wherein:

$R^a$, $R^b$, $R^c$ and $R^d$ are each independently selected from the group consisting of H, halo, $C_1$-$C_{20}$ alkyl, $C_1$-$C_{20}$ alkenyl, $C_1$-$C_{20}$ alkynyl, $C_1$-$C_{20}$ alkoxy, aryl, heteroaryl, keto, carboxy, amino, silyl, boron, and targeting groups;

or an adjacent pair of $R^a$ and $R^b$, $R^b$ and $R^c$, or $R^c$ and $R^d$ together form a substituent of the formula —O(CH$_2$)$_n$O—, where n is from 1 to 3; and $R^e$ is selected from the group consisting of H, $C_1$-$C_{20}$ alkyl, $C_1$-$C_{20}$ alkenyl, $C_1$-$C_{20}$ alkynyl, aryl, heteroaryl, keto, carboxy, and targeting groups;

$R^f$ and $R^g$ are each independently selected from the group consisting of consisting of H, $C_1$-$C_{20}$ alkyl, $C_1$-$C_{20}$ alkenyl, $C_1$-$C_{20}$ alkynyl, $C_1$-$C_{20}$ alkoxy, aryl, heteroaryl, keto, carboxy, amino, and targeting groups.

Preferably, at least one of $R^a$, $R^b$, $R^c$ and $R^d$ is $C_1$-$C_{20}$ alkoxy. Preferably, an adjacent pair of $R^a$ and $R^b$, $R^b$ and $R^c$, or $R^c$ and $R^d$ together form a substituent of the formula —O(CH$_2$)$_n$O—, wherein n is an integer from 1 to 3. Preferably, at least one of $R^a$, $R^b$, $R^c$ and $R^d$, $R^e$, $R^f$ and $R^g$ is a targeting group. Preferably, the compound is a phosphoramidite or N,N-dimethylamidophosphorochloridate.

An oligonucleotide or oligonucleotide analog compound containing a sequence of nucleotide or nucleotide analogs, wherein at least one of the nucleotides or nucleotide analogs is a caged nucleotide or nucleotide analog selected from the group consisting of:

(Purines:)

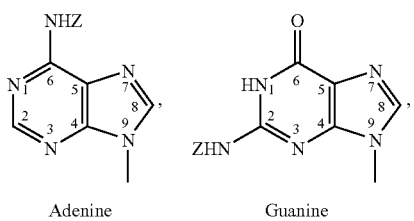

Adenine  Guanine (Pyrimidines:)

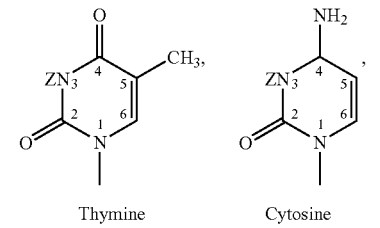

Thymine  Cytosine

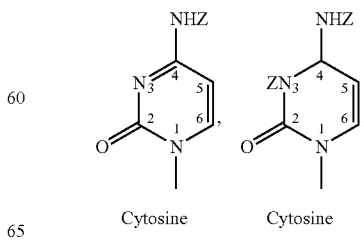

Cytosine  Cytosine  Uracil wherein Z is a caging group of the formula:

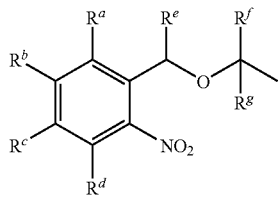

and wherein:

$R^a$, $R^b$, $R^c$ and $R^d$ are each independently selected from the group consisting of H, halo, $C_1$-$C_{20}$ alkyl, $C_1$-$C_{20}$ alkenyl, $C_1$-$C_{20}$ alkynyl, $C_1$-$C_{20}$ alkoxy, aryl, heteroaryl, keto, carboxy, amino, silyl, boron, and targeting groups;

or an adjacent pair of $R^a$ and $R^b$, $R^b$ and $R^c$, or $R^c$ and $R^d$ together form a substituent of the formula —O(CH$_2$)$_n$O—, where n is from 1 to 3; and $R^e$ is selected from the group consisting of H, $C_1$-$C_{20}$ alkyl, $C_1$-$C_{20}$ alkenyl, $C_1$-$C_{20}$ alkynyl, aryl, heteroaryl, keto, carboxy, and targeting groups;

$R^f$ and $R^g$ are each independently selected from the group consisting of consisting of H, $C_1$-$C_{20}$ alkyl, $C_1$-$C_{20}$ alkenyl, $C_1$-$C_{20}$ alkynyl, $C_1$-$C_{20}$ alkoxy, aryl, heteroaryl, keto, carboxy, amino, and targeting groups.

Preferably, at least one of $R^a$, $R^b$, $R^c$ and $R^d$ is $C_1$-$C_{20}$ alkoxy. Preferably, an adjacent pair of $R^a$ and $R^b$, $R^b$ and $R^c$, or $R^c$ and $R^d$ together form a substituent of the formula —O(CH$_2$)$_n$O—, wherein n is an integer from 1 to 3. Preferably, at least one of $R^a$, $R^b$, $R^c$ and $R^d$, $R^e$, $R^f$ and $R^g$ is a targeting group. Preferably, the compound is a phosphoramidite or N,N-dimethylamidophosphorochloridate.

The present disclosure further provides a method for deprotecting (or "decaging") an oligonucleotide or oligonucleotide analog, comprising the steps of:

(a) providing an oligonucleotide or oligonucleotide analog comprising a plurality of nucleotides or nucleotide analogs, in vitro or in vivo in a cell, tissue, or subject, wherein at least one of the nucleotides or nucleotide analogs is a caged nucleotide or nucleotide analog selected from the group consisting of:

(Purines:)

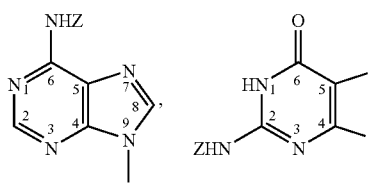

Adenine     Guanine (Pyrimidines:)

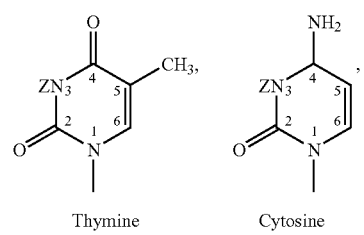

Thymine     Cytosine

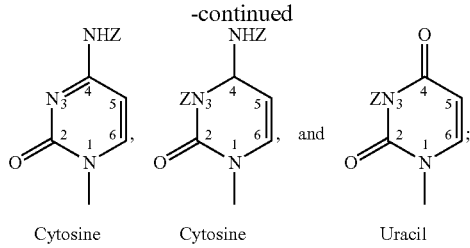

Cytosine    Cytosine    Uracil wherein Z is a caging group of the formula:

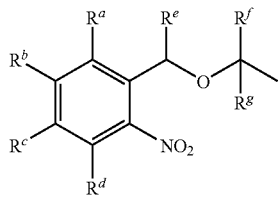

and wherein:

$R^a$, $R^b$, $R^c$ and $R^d$ are each independently selected from the group consisting of H, halo, $C_1$-$C_{20}$ alkyl, $C_1$-$C_{20}$ alkenyl, $C_1$-$C_{20}$ alkynyl, $C_1$-$C_{20}$ alkoxy, aryl, heteroaryl, keto, carboxy, amino, silyl, boron, and targeting groups;

or an adjacent pair of $R^a$ and $R^b$, $R^b$ and $R^c$, or $R^c$ and $R^d$ together form a substituent of the formula —O(CH$_2$)$_n$O—, where n is from 1 to 3; and $R^e$ is selected from the group consisting of H, $C_1$-$C_{20}$ alkyl, $C_1$-$C_{20}$ alkenyl, $C_1$-$C_{20}$ alkynyl, aryl, heteroaryl, keto, carboxy, and targeting groups;

$R^f$ and $R^g$ are each independently selected from the group consisting of consisting of H, $C_1$-$C_{20}$ alkyl, $C_1$-$C_{20}$ alkenyl, $C_1$-$C_{20}$ alkynyl, $C_1$-$C_{20}$ alkoxy, aryl, heteroaryl, keto, carboxy, amino, and targeting groups; and (b) exposing the oligonucleotide or oligonucleotide analog to light, whereby the caging group Z is cleaved from the base to thereby providing a deprotected or decaged oligonucleotide or oligonucleotide analog.

There is further disclosed a light inactivated oligonucleotide or oligonucleotide analog comprising a first self-hybridizing region, a region of interest coupled thereto, and optionally a second self-hybridizing region coupled thereto; wherein the first self-hybridizing region contains at least one caged pyrimdine or purine base having a caging group (Z) substituted thereon, wherein each of the at least one caged purine or pyrimidine bases is wherein at least one of the caged purine or pyrimidine bases is a caged nucleotide or nucleotide analog selected from the group consisting of:

(Purines:)

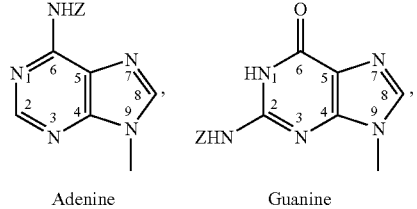

Adenine     Guanine

-continued (Pyrimidines:)

Thymine, Cytosine

Cytosine, Cytosine, and Uracil;

wherein Z is a caging group of the formula:

and wherein:

$R^a$, $R^b$, $R^c$ and $R^d$ are each independently selected from the group consisting of H, halo, $C_1$-$C_{20}$ alkyl, $C_1$-$C_{20}$ alkenyl, $C_1$-$C_{20}$ alkynyl, $C_1$-$C_{20}$ alkoxy, aryl, heteroaryl, keto, carboxy, amino, silyl, boron, and targeting groups;

or an adjacent pair of $R^a$ and $R^b$, $R^b$ and $R^c$, or $R^c$ and $R^d$ together form a substituent of the formula —O(CH$_2$)$_n$O—, where n is from 1 to 3; and $R^e$ is selected from the group consisting of H, $C_1$-$C_{20}$ alkyl, $C_1$-$C_{20}$ alkenyl, $C_1$-$C_{20}$ alkynyl, aryl, heteroaryl, keto, carboxy, and targeting groups;

$R^f$ and $R^g$ are each independently selected from the group consisting of consisting of H, $C_1$-$C_{20}$ alkyl, $C_1$-$C_{20}$ alkenyl, $C_1$-$C_{20}$ alkynyl, $C_1$-$C_{20}$ alkoxy, aryl, heteroaryl, keto, carboxy, amino, and targeting groups; whereby when the caging group is removed, the first self-hybridizing region hybridizes to either the region of interest or the second self-hybridizing region to form a hairpin and thereby mask the region of interest.

Thus, the present disclosure further provides a method for inactivating by decaging an oligonucleotide or oligonucleotide analog, comprising the steps of:

(a) providing (in vitro or in vivo) an oligonucleotide or oligonucleotide analog, wherein at least one of the caged purine or pyrimidine bases is a caged nucleotide or nucleotide analog selected from the group consisting of:

(Purines:)

Adenine, Guanine (Pyrimidines:)

Thymine, Cytosine

Cytosine, Cytosine, and Uracil;

wherein Z is a caging group of the formula:

and wherein:

$R^a$, $R^b$, $R^c$ and $R^d$ are each independently selected from the group consisting of H, halo, $C_1$-$C_{20}$ alkyl, $C_1$-$C_{20}$ alkenyl, $C_1$-$C_{20}$ alkynyl, alkoxy, aryl, heteroaryl, keto, carboxy, amino, silyl, boron, and targeting groups;

or an adjacent pair of $R^a$ and $R^b$, $R^b$ and $R^c$, or $R^c$ and $R^d$ together form a substituent of the formula —O(CH$_2$)$_n$O—, where n is from 1 to 3; and $R^e$ is selected from the group consisting of H, $C_1$-$C_{20}$ alkyl, $C_1$-$C_{20}$ alkenyl, $C_1$-$C_{20}$ alkynyl, aryl, heteroaryl, keto, carboxy, and targeting groups;

$R^f$ and $R^g$ are each independently selected from the group consisting of consisting of H, $C_1$-$C_{20}$ alkyl, $C_1$-$C_{20}$ alkenyl, $C_1$-$C_{20}$ alkynyl, $C_1$-$C_{20}$ alkoxy, aryl, heteroaryl, keto, carboxy, amino, and targeting groups; and (b) exposing the oligonucleotide or oligonucleotide analog to light.

Upon exposure to light the caging group Z is cleaved from the base to provide a deprotected or decaged oligonucleotide or oligonucleotide analog, causing the oligonucleotide to form a hairpin, and thereby inactivating the oligonucleotide or oligonucleotide analog.

DETAILED DESCRIPTION

A. Definitions

Figure 1:
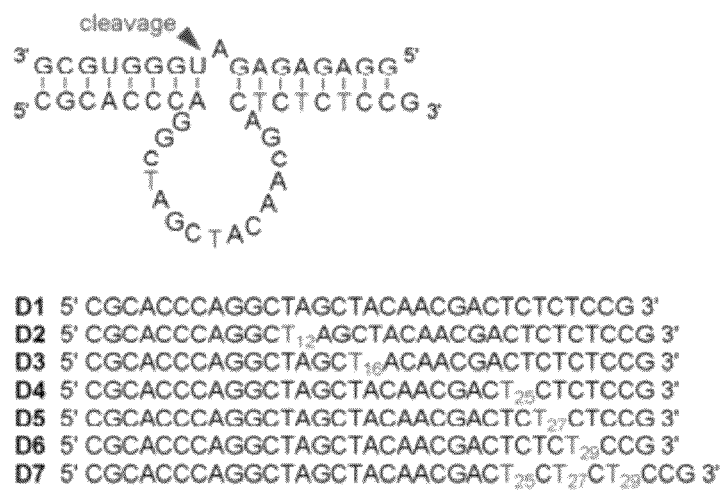
FIG. 1 shows 10-23 DNAzyme bound to its RNA substrate. Thymidines are highlighted in red. Wild-type DNAzyme D1 and DNAzymes D2-D7 have 1 incorporated at various thymidine positions.

"Caged" refers to a compound having a group thereon that substantially functionally inactivates the compound in at least one intended use thereon, and which group may be removed (e.g., by exposure to light in a "photocaged" compound) to restore activity of that compound.

"Nucleotide" refers to a monomeric unit of DNA or RNA containing (a) a purine (e.g., adenine, guanine) or pyrimidine (e.g., cytosine, thymine, uracil) base, (b) a pentose (2-deoxy-D-ribose in deoxyribonucleotides and D-ribose in ribonucleotides), and (c) a molecule of phosphoric acid. The pentose is joined to the base by a β-N-glycosyl bond between carbon atom 1 of the pentose and nitrogen atom 9 of purine bases or nitrogen atom 1 of pyrimidine bases. The phosphate group of nucleotides is in ester linkage with carbon atom 5 of the pentose. See, e.g., A. Leninger, *Biochemistry,* 309-312 (2d Ed. 1975).

"Nucleotide analog" includes nucleotides as described above in which the ribose or deoxyribose ring is altered, substituted or replaced, and/or where the phosphodiester bonds are altered, substituted or replaced (e.g., with a phosphorothioate group, a phosphoramidate group or the like. Examples are given in greater detail below.

"Oligonucleotide" refers to two more nucleotides linked by phosphodiester bridges formed between the 5'-hydroxyl group of one nucleotide and the 3'-hydroxyl group of the next adjacent nucleotide. A, Leninger, supra at 318. Oligonucleotides may be provided single stranded, double stranded with a complementary antiparallel oligonucleotide or oligonucleotide analog by Watson-Crick pairing (where the complementary strand may or may not contain a caged nucleotide or nucleotide analog as described herein), triplex or quadruplex stranded (e.g., as described in U.S. Pat. No. 6,656,692), etc. Oligonucleotides may be polymers of the same, or different, nucleotides, e.g., "gapamers".

"Oligonucleotide analog" refers to two or more nucleotide or nucleotide analogs (where at least one is a nucleotide analog), linked by phosphodiester bonds or other bond (such as a peptide bond for a peptide nucleic acid). Oligonucleotide analogs may be provided single stranded, double stranded with a complementary antiparallel oligonucleotide or oligonucleotide analog by Watson-Crick pairing (where the complementary strand may or may not contain a caged nucleotide or nucleotide analog as described herein), triplex or quadruplex stranded (e.g., as described in U.S. Pat. No. 6,656,692), etc. Oligonucleotide analogs may be polymers of the same, or different, nucleotide analogs or nucleotides, e.g., "gapamers".

"Halo refers to any suitable halogen, including —F, —Cl, —Br, and —I.

"Alkyl" refers to a straight or branched chain hydrocarbon containing from 1 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like.

"Lower alkyl" is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like.

"Alkenyl" refers to a straight or branched chain hydrocarbon containing from 2 to 20 carbons and containing at least one carbon-carbon double bond formed by the removal of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like.

"Lower alkenyl" is a subset of alkenyl and refers to a straight or branched chain hydrocarbon group containing from 1 to 4 carbon atoms.

"Alkynyl" refers to a straight or branched chain hydrocarbon group containing from 2 to 20 carbon atoms and containing at least one carbon-carbon triple bond. Representative examples of alkynyl include, but are not limited to, acetylenyl, 1-propynyl, 2-propynyl, 3-butynyl, 2-pentynyl, 1-butynyl and the like. "Lower alkynyl" as used herein, is a subset of alkyl and refers to a straight or branched chain hydrocarbon group containing from 1 to 4 carbon atoms.

"Alkoxy" refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like.

"Aryl" as used herein, refers to a monocyclic carbocyclic ring system or a bicyclic carbocyclic fused ring system having one or more aromatic rings. Representative examples of aryl include, for example, azulenyl, indanyl, indenyl, naphthyl, phenyl, tetrahydronaphthyl, and the like. The aryl groups can be substituted with 1, 2, 3, 4, or 5 substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, —NR'R" (wherein, R' and R" are independently selected from hydrogen, alkyl, alkylcarbonyl, aryl, arylalkyl and formyl), and —C(O)NR'R" (wherein R' and R" are independently selected from hydrogen, alkyl, alkylcarbonyl, aryl, arylalkyl, and formyl).

"Heteroaryl" means a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from O, N, and S. The heteroaryl group, including each heteroatom, can be unsubstituted or substituted with from 1 to 4 substituents, as chemically feasible. For example, the heteroatom S may be substituted with one or two oxo groups, which may be shown as =O.

"Keto" refers to a C(=O)R group, where R can be an alkyl, alkenyl, alkynyl, aryl, or heteroaryl group (as defined above).

"Carboxy" refers to a —COOR group, where R can be a proton, or an alkyl, alkenyl, alkynyl, aryl, or heteroaryl group (as defined above).

"Amino refers to a —NH$_2$ group, which may be unsubstituted or optionally substituted (that is, where one or two of the hydrogens is replaced by a suitable substituent such as alkyl, alkenyl, alkynyl, aryl, or heteroaryl group (as defined above)). Disubstituted amines may have substituents that are bridging, i.e., form a heterocyclic ring structure that includes the amine nitrogen.

"Silyl" refers to a SiR$_4$ group, where R can be an alkyl, alkenyl, alkynyl, aryl, or heteroaryl group (as defined above).

"Boron" refers to a B(OR)$_2$ group, where R can be an alkyl, alkenyl, alkynyl, aryl, or heteroaryl group (as defined above).

"Targeting group" as used herein may be any suitable targeting group, including but not limited to oligonucleotides, proteins, peptides, lectins, saccharides, etc. The targeting group may be covalently or non-covalently coupled to the compounds in accordance with known techniques or variations thereof that will be apparent to those skilled in the art. Targeting groups for the delivery of diagnostic and therapeutic agents, and their manner of coupling to other materials, are known and described in, for example, U.S. Pat. Nos. 7,259,138; 6,338,843; 5,780,054; 5,593,658; and 5,534,241. The targeting group may be one that binds to particular or specific tissues or cells, or pathological or diseased tissues or cells, such as inflamed tissue or cells, cancer tissue or cells, angiogenic tissue or cells, infectious microbial cells (such as bacterial, protozoal, fungal, or yeast cells), etc.

"Protecting group" includes any suitable protecting group; "protected form" refers to a substituent in which an atom such as hydrogen has been removed and replaced with a corresponding protecting group. Protecting groups are known. See generally T. H. Greene and P. G. M. Wuts, *Protective Groups in Organic Synthesis*, 3rd edition, John Wiley & Sons, New York (1999). Examples include but are not limited to: hydroxy protecting groups (for producing the protected form of hydroxy); carboxy protecting groups (for producing the protected form of carboxylic acid); amino-protecting groups (for producing the protected form of amino); sulfhydryl protecting groups (for producing the protected form of sulfhydryl); etc. Particular examples include but are not limited to: benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, di phenyl methoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, paramethoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl) ethoxymethyl, methanesulfonyl, para-toluenesulfonyl, trimethylsilyl, triethylsilyl, triisopropylsilyl, acetyl (Ac or —C(O)CH$_3$), benzoyl (Bn or —C(O)C$_6$H$_5$), and trimethylsilyl (TMS or —Si(CH$_3$)$_3$), and the like; formyl, acetyl, benzoyl, pivaloyl, t-butylacetyl, phenylsulfonyl, benzyl, t-butyloxycarbonyl (Boc), and benzyloxycarbonyl (Cbz) and the like; and hemithioacetals such as 1-ethoxyethyl and methoxymethyl, thioesters, or thiocarbonates and the like. See, e.g., U.S. Pat. Nos. 6,953,782; 6,951,946; 6,951,942; and 6,051,724.

"Activated phosphorous groups include, but are not limited to, phosphoramidate groups. Such groups are known and described in, for example, U.S. Pat. Nos. 7,087,732; 7,217,805; 6,605,611; 6,531,589; and 5,552,400. Examples include, but are not limited to, N,N-dialkyl-O-methylphosphoramidite, phosphochloridite, H-phosphonate, and a N,N-dialkyl-O-(2-cyanoethyl)phosphoramidite groups.

B. Nucleotides and Nucleotide Analogs

Any nucleotide (sometimes also referred to as a "nucleic acid") or nucleotide analog (sometimes also referred to as a "nucleic acid analog") can be used. The most common examples of nucleotides that can be used include, but are not limited to, for ribonucleotides: adenosine 5'-phosphoric acid; guanosine 5'-phosphoric acid; cytidine 5'-phosphoric acid, and uridine 5'-phosphoric acid; and for deoxyribonucleotides, deoxyadenosine 5'-phosphoric acid, deoxyguanosine 5'-phosphoric acid, deoxycytidine 5'-phosphoric acid, and deoxythymidine 5'-phosphoric acid. See, e.g., A. Leninger, *Biochemistry*, 309-312 (2d Ed. 1975).

Examples of nucleotide analogs that may be used include, but are not limited to: a peptide nucleic acid, pyranosyl-RNA, a hexitol nucleic acid, a mannitol nucleic acid, an altritol nucleic acid, a 2',5'-nucleic acid, a locked nucleic acid, a seco-locked nucleic acid, a bicyclic nucleic acid such as a bicyclo[3.2.1]DNA or a bicyclo[3.3.0]DNA, a tricyclic nucleic acid such as a tricyclo-DNA, 3-hydroxy-N-acetylprolinol substituted nucleic acid, a carbocyclic nucleic acid, a carbocyclic/bicyclic nucleic acid, a nucleic acid with a triazole backbone, a nucleic acid with an imidazole backbone, a 1-phenylserinol nucleic acid, a nucleic acid with an alpha-anomeric backbone, and a metal-linked nucleic acid (See, e.g., U.S. Pat. No. 7,071,324). Additional examples of nucleotide analogs include, but are not limited to, a morpholino nucleic acid (see U.S. Pat. No. 5,698,685, incorporated by reference herein), a cyclohexenyl nucleic acid, an anhydrohexitol nucleic acid, a phosphonomonoester nucleic acid, a cyclobutyl nucleic acid (See, e.g., U.S. Pat. No. 6,878,805, incorporated by reference herein), and a piperazine nucleic acid (see, e.g., U.S. Pat. No. 6,841,675, incorporated by reference herein). Additional examples of nucleotide analogs include, but are not limited to, a phosphorothioate nucleic acid, a 2'-O-alkyl nucleotide (e.g., 2'-O-methyl RNA, a 2'-O-methoxy-ethyl RNA), a fluoro-arabinose nucleic acid (see, e.g., U.S. Patent Application 2006/0057595, incorporated by reference herein), a phosphorothioate nucleic acid, an N3'-P'5 phosphoroamidate nucleic acid (see, e.g., J. Kurreck, *Eur. J. Biochem.* 27, 1628-1644 (2003); see also S. Verma, and F. Eckstein, Modified oligonucleotides: Synthesis and strategy for users. *Annu. Rev. Biochem.* 67: 99-134 (1998)).

Specific examples of nucleotides and nucleotide analogs that can be used include, but are not limited to:

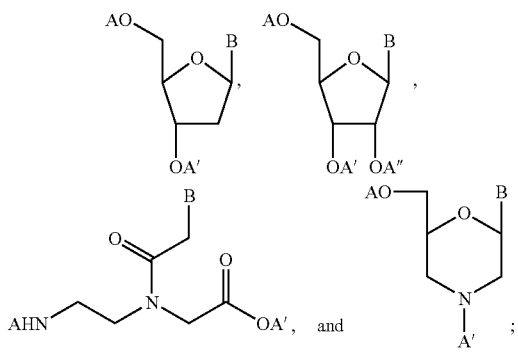

wherein:

A, A' and A" are each independently H or a protecting group, or A' is a activated phosphorous group such as a phosphoramidite group; and B is the purine or pyrimidine base.

C. Oligonucleotides and Oligonucleotide Analogs

Oligonucleotides and oligonucleotide analogs can be prepared by enzymatic or chemical synthesis in accordance with known techniques such as the phosphoramidite method. Typically, in phosphoramidite synthesis, oligonucleotides are prepared by solid phase synthesis with protection chemistry where the most reactive groups are protected to avoid unwanted products. For example, a 3' primer is immobilized on a solid support such as a polystyrene bead with a suitable linker, while the 5' hydroxyl group is protected with a dimethoxytrityl (DMT) group or another suitable protecting group. The free phosphoramidite bases typically have on their phosphate group a diisopropylamino group and a 2-cyanoethyl group. The bases also have protecting groups on the exocyclic amine groups (e.g., benzoyl or isobutyryl). The oligonucleotide or oligonucleotide analog synthesis proceeds through the steps of: (i) Detritylation: the DMT is removed with an acid, such as trichloroacetic acid, resulting in a free OH; (ii) Coupling: a phosphoramidite nucleotide or nucleotide analog is added (or a mix) and tetrazole which removes the iPr$_2$N group on the incoming base that is attacked by the deprotected 5' OH of the growing oligo (these reactions are not done in water but in acetonitrile, tetrahydrofuran or DMSO). In RNA the 2' is protected with a TBS (butyldimethylsilyl) group or with a Me group; (iii) Capping: the few (1%) free 5'OH groups must be blocked; they are capped with acetic anhydride and 1-methylimidazole; and (iv) Oxidation: the phosphate group is made pentavalent by adding iodine and water. This step can be substituted with a sulphurylation step for thiophosphate nucleotides. These 4 steps are repeated n number of times. The products are cleaved and deprotected (base and phosphate) via base mediated hydrolysis (ammonium hydroxide). They are then desalted and lyophilized or purified by HPLC. Reporter groups and the like can optionally be added post-synthesis (aminoallyl groups are a common method). See generally WIKIPEDIA at "Phosphoramidite"; See, also T. Brown DJS. 1991. In Oligonucleotides and Analogues. A Practical Approach, ed. F Eckstein, pp. 1-24. Oxford: IRL (1991); For longer oligonucleotides, shorter oligonucleotides prepared by methods such as described above can be linked enzymatically, e.g., with T4 RNA ligase, T4 DNA ligase, or T7 polymerase with template-driven enzymatic synthesis.

Numerous examples of the synthesis of oligonucleotides and oligonucleotide analogs which can be used, and numerous practical uses for such oligonucleotides, are known. See, e.g., U.S. Pat. Nos. RE39,464; 7,297,479; 7,202,264; 7,169,939; 7,138,517; 6,987,177; 6,849,230; 6,518,017; 6,426,407; 6,274,725; 6,033,909.

In general, oligonucleotides or oligonucleotide analogs (e.g., "light activated" oligonucleotides or oligonucleotide analogs) are from 2 or 5 monomeric units (e.g., nucleotides) in length, up to 20, 30, 100, 200, 1000 or even 5000 or more monomeric units in length, with longer lengths typically being achieved by enzymatic ligation of shorter segments. The oligonucleotide or oligonucleotide analog will typically contain at least 1 or 2 caged purine or pyrimidine bases as described above, up to 50 or 100 caged purine or pyrimidine bases (or up to 30 or 50 percent of the total number of purine or pyrimidine bases being caged purine or pyrimidine bases as described herein, depending upon the length and purpose of the oligonucleotide or oligonucleotide analog.

In general, "light inactivated" oligonucleotides or oligonucleotide analogs comprise, consist of or consist essentially of a first self-hybridizing region (e.g., ten to 50 monomeric units in length), a region of interest (e.g., 10 to 50 nucleotides in length) coupled thereto (e.g., by phosphodiester bond or other linkage appropriate for the particular oligonucleotide or oligonucleotide analog to form a continuous polymer), and optionally a second self-hybridizing region (e.g., 10 to 50 nucleotides in length) coupled (in like manner as above) thereto. The region of interest can encode a probe, primer, siRNA, catalyst or enzyme, or any other functional molecule as described for "light activated" oligonucleotides as described herein. The first self-hybridizing region contains at least one caged purine or pyrimidine base having a caging group substituted thereon as described above, and in some embodiments contains from 2 to 5 caged purine or pyrimidine bases as described above (and preferably all of which are the same). When the caging group or groups are subsequently removed (e.g., by self exposure to light as discussed further below), said first self-hybridizing region hybridizes (by intentional design to achieve Watson-Crick pairing) to either the region of interest or the second self-hybridizing region to form a hairpin (it being appreciated that, in some embodiments, the region of interest and the second self-hybridizing region can partially overlap). Hairpin formation "masks" the region of interest, or makes it functionally unavailable for its intended purpose, to thereby "light inactivate" the oligonucleotide or oligonucleotide analog.

D. Use

Oligonucleotides are useful as oligonucleotide probes, oligonucleotide primers (e.g., for nucleic acid amplification procedures such as polymerase chain reaction, ligase chain reaction, strand displacement amplification, etc.), as small interfering RNAs (siRNAs), as antisense oligonucleotides, as sensors or aptamers, as riboswitches or antiswitches, as catalysts or enzymes such as DNAzymes and ribozymes, etc., wherever light activation or light inactivation in the course of the use of the oligonucleotide would be advantageous (e.g., once a reaction has proceeded to a particular course, when activation or inactivation is desired in a particular target location, when temporal protection of the oligonucleotide against restriction endo- and exonucleases, polymerases and the like is desired, etc.). Oligonucleotides and oligonucleotide analogs of the invention can be used in synthetic regulatory elements such as promoters, enhancers, and synthetic genes in recombinant nucleic acids for expression of a protein or peptide when light activation is desired.

Generally, spatial and temporal control of the function of oligonucleotides and oligonucleotide analogs, as described herein, can be achieved in vitro (e.g., in a nucleic acid amplification system such as PCR or a diagnostic assay) and in vivo (e.g., as antisense agents for the regulation of gene function). When used in vivo, the method can be carried out by administering or contacting the oligonucleotide or oligonucleotide analogs to cells (e.g., cells in culture), tissue (e.g., tissue in culture, such as muscle, skin, liver, nerve, bone, or pancreatic tissue, etc.), or administering to a subject (e.g., a human or animal subject, including but not limited to fish, bird, reptile amphibian, or mammalian subjects). Mammalian subjects include but are not limited to human, mouse, cow, horse, pig, sheep, goat, rabbit, rat, cat, dog, etc. Subjects may be at any stage of development including prenatal, neonatal, infant, juvenile, adolescent, adult, and geriatric. Cells, tissues, and subjects include non-animals as well, such as plant (including angiosperm and gymnosperm), yeast, fungi, and bacterial cells, tissues, and subjects.

For exposing the compounds to light, whether in vivo or in vitro, the light may be of any suitable wavelength and intensity, with UV light (particularly UV light of 365 nm) currently preferred.

In some embodiments, the exposing step is carried out by "two-photon decaging" in accordance with known two-photon excitation techniques. See, e.g., U.S. Pat. Nos. 7,049,480; 6,020,591; and 5,034,613. In some embodiments, two photons of a suitable wavelength (e.g., equal to or greater than 650 or 700 nm) are directed at the caged oligonucleotide with approximately a 100 femtosecond pulse width and an approximately 80 MHz repetition rate, where they then double up and remove the caging group. Two photon decaging can if desired be facilitated through the use of a two-photon sensitizer. This is an important technique, because photons of such wavelengths can be focused more precisely and penetrate tissue more deeply.

Oligonucleotides and oligonucleotide analogs can be prepared as physiologically or pharmaceutically acceptable formulations and administered to cells, tissues or subjects in like manner as other oligonucleotides and oligonucleotide analogs, and for the same physiological or therapeutic purposes (see, e.g., U.S. Pat. Nos. 7,273,932; 7,262,175; 7,108,844; 7,098,192; 7,074,915; 7,030,236; 6,841,539; 6,809,193), with the added feature of light activation or inactivation at the desired point in time as noted above.

The oligonucleotide and oligonucleotide analogs (also referred to as "active compounds") described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations of the present invention suitable for parenteral administration comprise sterile aqueous and non-aqueous injection solutions of the active compound(s), which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline. Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient. Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques. Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

The therapeutically effective dosage of any specific active compound, will vary somewhat from compound to compound, and subject to subject, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed.

In one embodiment of the present disclosure, a photochemical activation and deactivation of the polymerase chain reaction, of light-activation of DNAzymes, of PS DNA antisense agents, and of morphilino antisense agents have been developed. This was achieved through the experiments outlines in the examples below and by incorporation of caged thymidine phosphoramidites into oligonucleotide primers using standard DNA synthesis protocols. By effectively disrupting DNA hybridization through the site-specific installation of caging groups and restoring it with light irradiation it was possible to control activation and deactivation of PCR in a temporal fashion. Moreover, by conducting a simultaneous activation and deactivation, light switching from one DNA amplification product to another was accomplished. Non-specific amplification of DNA was prevented by caged PCR primers.

Example 1

NPOM Caged Thymidine Phosphoramidite and Photochemical DNA Activation

The developed caging approach fulfills all of the following requirements: a) allows for specific probing of hydrogen bonding of oligonucleotide bases, b) enables introduction of the caged monomer under standard DNA synthesis conditions, c) provides a caged oligomer which is stable to a wide range of chemical and physiological conditions, and d) allows for excellent restoration of DNA activity upon brief irradiation with non-photodamaging UV light. Recently, a new caging group (NPOM=6-nitropiperonyloxymethyl) was developed which proved to be highly efficient in the caging of nitrogen heterocycles (H. Lusic and A. Deiters, *Synthesis* 2006, 2147). This group was specifically designed to solve previous problems associated with chemical stability or slow decaging rates of photo-protecting groups on nitrogen atoms. This example provides the application of this group to the caging of the thymidine N-3, thus disrupting an essential hydrogen bond. The phosphoramidite 1 (Scheme 1) was synthesized in 5 steps from thymidine starting with the preparation of the known acetylated thymidine 2 (Ac$_2$O, DMAP, 98%) (R. Saladino et al., *Tetrahedron* 1995, 51, 3607). Caging with 6-nitropiperonyloxymethyl chloride (NPOM-Cl)[12] was achieved in 82% (Cs$_2$CO$_3$, DMF, rt) yielding 3. Removal of the actetate groups (K$_2$CO$_3$, MeOH, 78%) towards 4 followed by selective tritylation of the primary hydroxy group (DMTCl, DMAP, pyridine) delivered 5 in 91% yield. Installation of the phosphoramidite (2-cyanoethyl-diisopropyl-chloro phosphoramidite, DCM DIPEA) was achieved in 80% under classical conditions completing the synthesis of 1.

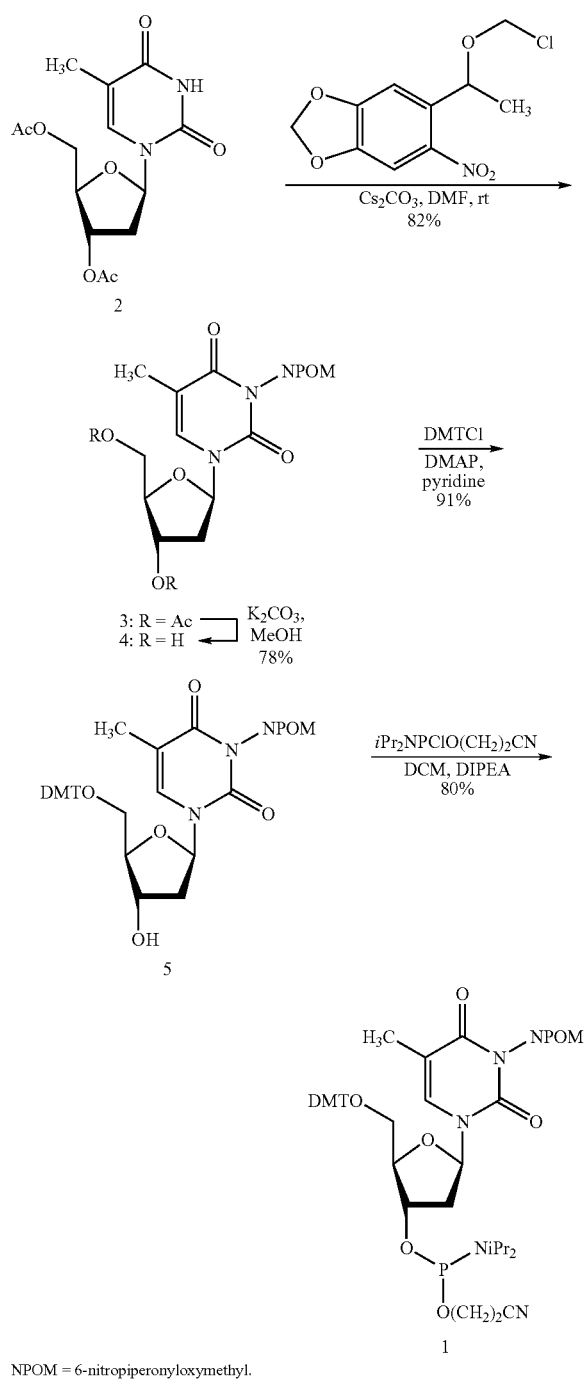

Scheme 1. Synthesis of the caged phosphoramidite 1.

NPOM = 6-nitropiperonyloxymethyl.

The stability of 1 to DNA synthesis conditions and its rapid decaging through irradiation with UV light of 356 nm ($\epsilon_{365}$=6887 cm$^{-1}$M$^{-1}$) was demonstrated. The quantum yield ($\phi$=0.094) for the photochemical removal of the NPOM group was determined by 3,4-dimethoxynitrobenzene actinometry (J. Zhang et al., *Appl. Surf. Sci.* 1999, 139, 315; L. Pavlickova et al., *Collect. Czech. Chem. Commun.* 1986, 51, 368). Using standard DNA synthesis conditions 1 has been incorporated at all thymidine positions of the 10-23 DNAzyme D1 providing the mutants D2-D7 (FIG. 1). The 10-23 DNAzyme is a highly active and sequence specific RNA cleaving deoxyoligonucleotide (S. Santoro and G. Joyce, *Biochemistry* 1998, 37, 13330). It has been successfully applied to the suppression of genes in vitro and in model organisms (M. Cairns et al., *Curr. Drug. Targets* 2002, 3, 269).

Figure 2:
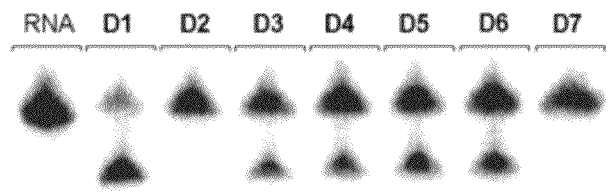
FIG. 2 shows cleavage of the RNA substrate for 30 min with the 10-23 DNAzymes D1-D7 without prior UV irradiation in 100 mM $MgCl_2$, pH 8.2, 15 mM Tris buffer, 37° C., 40 nM substrate, 400 nM enzyme.

To probe the necessity of free 3-NH groups in these thymidine residues for the maintenance of DNAzyme activity, the RNA substrate 5'-GGAGAGAGAUGGG-UGCG-3' [SEQ ID NO. 1] was radioactively 5'-labeled using $^{32}$P-ATP and exposed to the seven DNAzymes D1-D7 in a standard reaction buffer (100 mM MgCl$_2$, pH 8.2, 15 mM Tris buffer) for 30 min at 37° C. (FIG. 2). As expected, the original 10-23 DNAzyme D1 led to almost complete RNA cleavage. DNAzyme D2 exhibited completely inhibited activity due to the installation of a single caging group on $T_{12}$. This was expected, since a previous mutagenesis study of the catalytic core revealed this to be an essential residue (Z. Zaborowska et al., *J. Biol. Chem.* 2002, 277, 40617). These experiments also demonstrated that the least essential thymidine residue is located at position 16. This was confirmed through the incorporation of 1 at this position leading to still catalytically active D3, even in presence of the sterically demanding caging group.

We then probed the tolerance of base pair mismatches in the substrate recognition domains by caging the thymidine residues $T_{25}$, $T_{27}$, and $T_{29}$. The resulting DNAzymes D4-D6 displayed lower activity but still induced substantial RNA cleavage. Previously, single mismatches between the RNA substrate and the flanking regions have led to reduced cleavage activity as well. However, selective installation of three caging groups on $T_{25}$, $T_{27}$, and $T_{29}$ lead to complete inhibition of RNA cleavage activity in D7, presumably due to the disruption of multiple Watson-Crick base paring interactions with the substrate.

Figure 3:
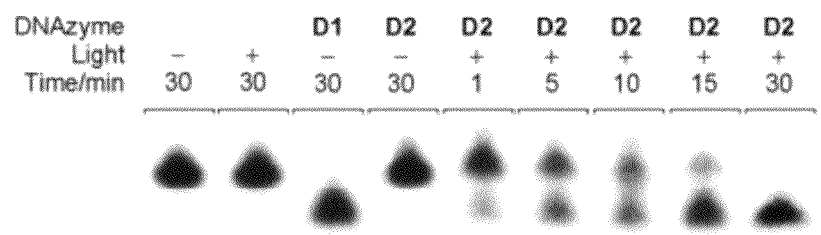
FIG. 3 shows progressing cleavage of the RNA substrate with the 10-23 DNAzyme D2 after a 1 min UV irradiation (365 nm). Complete RNA cleavage was observed after 30 min in 100 mM $MgCl_2$, pH 8.2, 15 mM Tris buffer, 37° C., 40 nM substrate, 400 nM enzyme.

Subsequently, a more detailed time-course investigation of the light-activation of D2 was conducted (FIG. 3). A control experiment of just the RNA substrate exposed to UV light did not result in any cleaved product. Complete cleavage of the RNA substrate was achieved within 30 min using the unmodified D1, whereas no cleavage was observed with caged D2 under identical conditions. However, brief irradiation with non-photodamaging UV light of 365 nm (25 W) for 1 min initiated decaging and activation of D2. FIG. 3 displays the resulting RNA cleavage with complete consumption of the substrate by 30 min.

Figure 4:
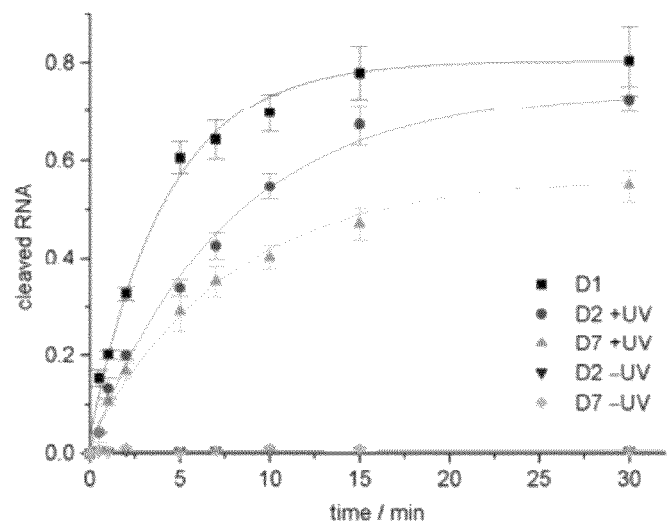
FIG. 4 shows cleavage of the RNA substrate with the wild-type DNAzyme D1 and the caged DNAzymes D2 and D7 (with and without UV irradiation) in 10 mM $MgCl_2$, pH 7.4, 15 mM Tris buffer, 37° C., 40 nM substrate, 400 nM enzyme. The cleaved RNA had been normalized and the experiments were conducted in triplicate.

In order to determine the cleavage rates k of the DNAzymes D1, D2, and D7, the amount of cleaved RNA was quantified at nine different time points under single-turnover conditions through integration (using Molecular Dynamics ImageQuant 5.2™) of the corresponding radioactive bands in 15% denaturing TBE polyacrylamide gels using a PhosphorImager (FIG. 4).

The data was fitted (using Microcal Origin 5.0™) with an exponential decay curve $\sim\mathrm{-e}^{kt}$) (M. Cairns et al., *Nucleic. Acids. Res.* 2003, 31, 2883), and, as previously observed, the wild-type DNAzyme D1 showed a high cleavage rate ($k_{D1}$=0.242±0.013 min$^{-1}$) under the assay conditions. As expected from the results shown in FIG. 2, the caged DNAzymes D2 and D7 displayed no cleavage activity ($k_{D2}$=ND and $k_{D7}$=ND), demonstrating that caging group installation on thymidine can completely abrogate both catalytic activity and substrate binding. Gratifyingly, brief irradiation for 1 min (365 nm, 25 W) of the caged DNAzymes led to restoration of catalytic activity of D2 ($k_{D2,UV}$=0.131±0.007 min$^{-1}$) and D7 ($k_{D7,UV}$=0.129±0.011 min$^{-1}$) to 54% and 53% of the original D1 activity, respectively. After a 30 min incubation time 80% of the RNA substrate was cleaved by D1, 73% by irradiated D2, and 55% by irradiated D7. Thus DNAzymes with an excellent light-triggered switch have been developed.

Synthesis of the caged thymidine phosphoramidite 1. The synthesis of the caged thymidine phosphoramidite 1 is depicted in Scheme 1. All reaction vessels were wrapped in aluminum foil; however, no special precautions to exclude light during chromatography were taken.

Acetate 2. Thymidine (1.0 g, 4.10 mmol), DMAP (spatula tip) and $Ac_2O$ (5 mL) were stirred under nitrogen until all the solid disappeared. Excess $Ac_2O$ was evaporated in vacuo and the residue was dissolved in 100 mL of DCM. The organic layer was washed with 2×100 mL of water, 100 mL of $NaHCO_3$, and brine. The organic layer was dried over $MgSO_4$, filtered and evaporated. The acetate 2 was obtained as a white, solid foam in 98% yield (1.3 g, 4.0 mmol). Its analytical data was identical with the literature (Saladino, R.; Crestini, C.; Occhionero, F.; Nicoletti, R., *Tetrahedron* 1995, 51, 3607).

Caged acetate 3. $Cs_2CO_3$ (300 mg, 0.90 mmol) was added to a stirred solution of compound 2 (100 mg, 0.30 mmol) in DMF (1 mL). The mixture was stirred for 1 h at room temperature. The reaction mixture was then cooled to 0° C. NPOM-Cl (120 mg, 0.46 mmol, dissolved in 0.5 mL of DMF) was added dropwise to the reaction mixture and stirring was continued for 12 h at room temperature. EtOAc (15 mL) was added and the organic layer was washed with 2×15 mL of water, followed by a wash with 15 mL of a saturated $NaHCO_3$ solution. The organic layer was dried over $MgSO_4$ and the solvent was evaporated in vacuo. Purification by silica gel chromatography using hexanes:EtOAc (1:1) with 1% TEA as the eluent afforded 3 as a white foam in 82% yield (139 mg, 0.25 mmol). $^1$H NMR ($CDCl_3$) δ=1.49 (1.5H, s), 1.51* (1.5H, s), 1.87 (1.5H, s), 1.89* (1.5H, s), 2.08 (1H, m), 2.12 (6H, s), 2.50 (1H, m), 4.23 (1H, m), 4.35 (2H, m), 5.16-5.43 (4H, m), 6.07 (2H, m), 6.22 (1H, m), 7.12-7.26 (2H, m), 7.39 (0.5H, s), 7.42* (0.5H, s). $^{13}$C NMR ($CDCl_3$) δ=13.5, 21.0, 21.1, 23.9, 37.8, 63.9, 69.8, 73.3, 74.1, 82.3, 85.6, 102.9, 104.8, 106.6, 110.8, 133.1, 137.8, 142.1, 146.8, 150.7, 150.7, 152.1, 162.8, 170.1, 170.4. ESI-MS [M+Na]$^+$ m/z=572.1.

Caged thymidine 4. $K_2CO_3$ (100 mg, 0.72 mmol) was added to a stirred solution of compound 3 (100 mg, 0.18 mmol) in MeOH (2 mL). The reaction was stirred for 12 h at room temperature. The mixture was then filtered and the filtrate was concentrated in vacuo. Purification by silica gel chromatography using EtOAc:MeOH (90:10) with 1% TEA, afforded the product 4 as a white foam in 78% yield (66 mg, 0.14 mmol). $^1$H NMR (DMSO-d6)$^2$ δ=1.39 (3H, m), 1.69 (3H, m), 1.94-2.08 (2H, m), 3.56 (2H, m), 3.77 (1H, m), 4.20 (1H, m), 5.02-5.36 (5H, m), 5.98-6.20 (3H, m), 7.00 (1H, s), 7.45 (0.5H, s), 7.47* (0.5H, s), 7.58 (0.5H, s), 7.65* (0.5H, s). $^{13}$C NMR (DMSO-d6) δ=12.6, 23.6, 40.3, 61.2, 69.6, 70.2, 73.2, 84.6, 87.4, 103.4, 104.0, 105.6, 108.4, 134.9, 137.4, 141.0, 146.4, 149.9, 151.6, 162.3. ESI-MS [M+Na]$^+$ m/z=488.1.

Trityl ether 5. DMAP (spatula tip) and dimethoxytrityl chloride (86 mg, 0.26 mmol) were added to a stirred solution of the caged thymidine (4) (100 mg, 0.2 mmol) in pyridine (1 mL). The reaction was stirred for 12 h at room temperature. Saturated $NaHCO_3$ (10 mL) was added, and the mixture was extracted with 3×10 mL of EtOAc. The combined organic layers were dried over $Na_2SO_4$ and the solvent was evaporated in vacuo. The residue was purified by silica gel chromatography using DCM and 3% TEA as the eluent, yielding 5 in 91% yield (150 mg, 0.18 mmol) as a yellow foam. $^1$H NMR (DMSO-d6) δ=1.28-1.42 (6H, m), 2.15 (2H, m), 3.19 (2H, m), 3.74, (6H, m), 3.91 (1H, m), 4.25-4.34 (1H, m), 5.12 (2H, m), 5.34 (2H, m), 6.04-6.18 (3H, m), 6.88 (4H, d), 7.02 (1H, s), 7.21-7.46 (10H, m). $^{13}$C NMR (DMSO-d6) δ=12.0, 23.6, 40.2, 55.0, 63.7, 69.7, 70.3, 73.1, 84.5, 85.6, 85.8, 103.2, 103.8, 105.6, 108.6, 113.1, 126.6, 127.5, 127.7, 129.5, 135.0, 135.9, 137.4, 140.8, 144.4, 146.4, 149.4, 151.4, 157.9, 162.2. FAB-HRMS [M]$^+$ m/z for $C_{41}H_{41}N_3O_{12}$: calcd: 767.2690. Found: 767.2715.

Caged thymidine phosphoramidite 1. DIPEA (118 mg, 0.91 mmol) and 2-cyanoethyl-diisopropyl-chloro phosphoramidite (108 mg, 0.45 mmol) were added to a stirred solution of 5 (100 mg, 0.13 mmol) in DCM (2 mL). The reaction was stirred for 1 h at room temperature and subsequently quenched by the addition of MeOH (0.2 mL). The volatiles were evaporated in vacuo and the residue was purified by silica gel chromatography using hexanes:EtOAc (66:33) and 3% TEA as the eluent. The phosphoramidite 1 was obtained as a white foam in 80% yield (100 mg, 0.10 mmol). $^1$H NMR ($CDCl_3$) δ=1.05-1.58 (18H, m), 2.22 (1H, m), 2.42-2.66 (3H, m), 3.30-3.70 (6H, m), 3.79 (6H, s), 4.16 (1H, m), 4.61 (1H, m), 5.19-5.47 (3H, m), 6.05 (2H, m), 6.30 (1H, m), 6.83 (4H, m), 7.19-7.54 (12H, m). $^{13}$C NMR ($CDCl_3$) δ=12.6, 20.6, 23.9, 24.7, 24.9, 40.3, 43.4, 43.6, 55.5, 58.4, 63.4 69.6, 72.9, 73.9, 85.8, 85.7, 87.1, 102.9, 104.7, 106.6, 110.6, 113.4, 117.5, 127.2, 128.0, 127.2, 130.2, 134.2, 135.4, 138.2, 141.9, 144.3, 146.9, 150.7, 152.1, 158.8, 163.2. $^{31}$P NMR ($CDCl_3$, $H_3PO_4$ as internal standard) δ=148.9, 149.4, 149.5.

Example 2

NPOM Caged Deoxyguanosine Phosphoramidite

To complement the caged thymidine 1 we also synthesized the NPOM caged deoxyguanosine phosphoramidite dG5 (Scheme 2A). The synthesized O-acetylated and N-DMF protected nucleoside dG1 was reacted with NPOM chloride in 79% yield in the presence of DBU. Subsequent removal of the acetyl groups in dG2 and installation of a DMT group on the 5'-OH of dG3 proceeded in 92% and 77% yield, respectively. The synthesis of dG5 was completed by phosphorylation in 82% yield. Decaging experiments revealed an efficient removal of the NPOM group under UV irradiation (365 nm) identical to 1 (Lusic, H.; Lively, M. O., Deiters, A. *Mol. Bio Sys.* 2008, 4, 508).

Scheme 2A. Synthesis of the NPOM caged deoxyguanosine phosphoramidite dG5.

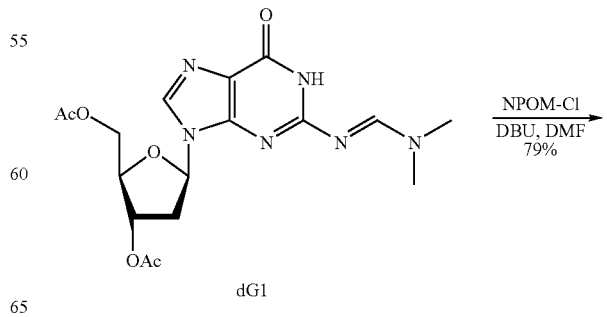

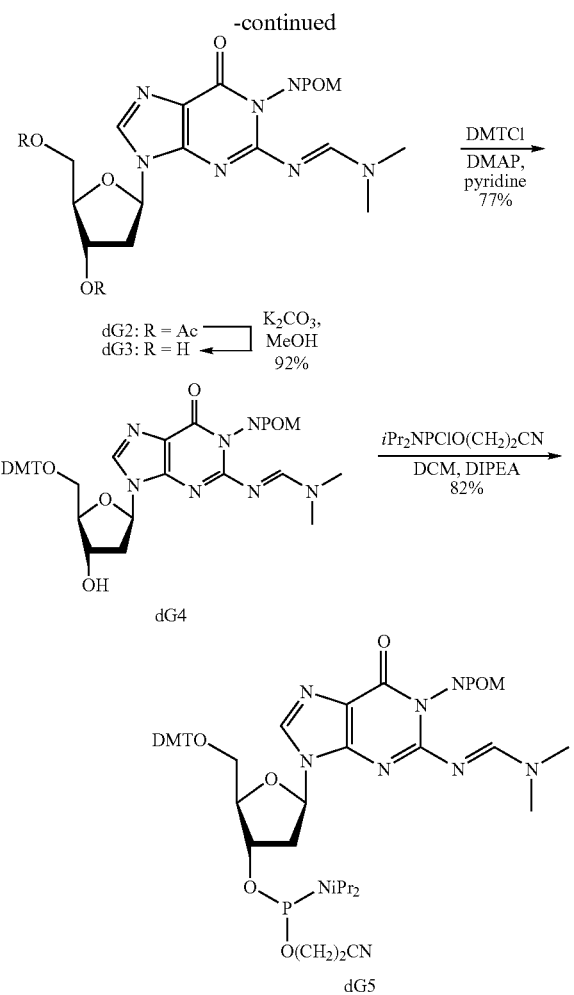

2'-Deoxy-3',5'-diacetate-N²-dimethylaminomethylene-guanosine (dG1). To 2'-deoxyguanosine (2 g, 7.5 mmol) suspension in dry MeOH (30 mL) was added N,N-Dimethylformamide dimethyl acetal (4 mL, 30 mmol). The reaction was refluxed for 5 h and the solvent subsequently evaporated. The residue was re-dissolved in pyridine (20 mL) and catalyst. DMAP and AcOAc (2.8 mL, 30 mmol) were added to the solution. The reaction was stirred at room temperature for 8 h. The solvents were evaporated and the residue purified by silica gel chromatography using $CHCl_3$:MeOH (90:10) with 2% TEA, affording 1.86 g of dG1 as a white foam (61% yield). $^1$H NMR (CDCl3): δ=2.02 (s, 3H), 2.10 (s, 3H), 2.50 (m, 1H). 2.95-3.05 (m, 4H), 3.17 (s, 3H), 2.95-3.20 (m, 3H), 5.30 (m, 1H), 6.21 (t, J=6.9 Hz, 1H), 7.66 (s, 1H), 8.60 (s, 1H), 9.91 (s, 1H). $^{13}$C NMR (CDCl3): δ=20.9, 21.1, 35.5, 37.0, 41.5, 63.9, 74.3, 82.2, 84.3, 121.3, 136.9, 150.1, 157.2, 158.3, 158.4, 170.6, 170.8. HRMS-LC: m/z [M+H]⁺ calcd for $C_{13}H_{19}N_3O_6$: 314.1352. Found: 314.1347.

2'-Deoxy-3',5'-diacetate-N²-dimethylaminomethylene-N¹-(6-nitropiperonyloxymethylene)-guanosine (dG2). To compound dG1 (100 mg, 0.25 mmol) in DMF (1 mL) was added DBU (55 μL, 0.38 mmol) and the solution was stirred for 30 minutes at room temperature. To the solution was then added 6-nitropiperonylchloromethyl ether (1) (97 μL, 0.38 mmol) dissolved in DMF (0.5 mL) and the reaction was stirred at room temperature for 8 h. The reaction was diluted with EtOAc (10 mL) and washed with sat. $NaHCO_3$, $H_2O$ and brine (10 mL of each). The organic layer was dried over Na2SO4, filtered and the solvent was evaporated. Purification by silica gel chromatography using $CHCl_3$ with 2% TEA afforded 124 mg of compound dG2 as a yellow foam (79% yield). $^1$H NMR (CDCl₃): δ=1.43 (d, J=6.3 Hz, 3H), 2.05 (s, 3H), 2.11 (s, 3H), 2.42-2.51 (m, 1H), 2.95-3.07 (m, 4H), 3.20 (s, 3H), 4.16-4.38 (m, 3H), 5.33-5.49 (m, 2H), 5.68 (m, 1H), 5.82-5.94 (m, 3H), 6.14 (m, 1H), 7.14 (m, 1H), 7.29 (s, 1H), 7.60 (m, 1H), 8.36 (m, 1H). $^{13}$C NMR (CDCl₃): δ=20.9, 21.2, 24.1, 35.5, 36.8, 37.2, 41.5, 71.7, 73.9, 74.4, 82.1, 84.1, 103.0, 104.6, 107.2, 120.8, 136.5, 136.7, 139.3, 141.1, 146.8, 147.8, 152.5, 157.1, 157.8, 170.5, 170.8. HRMS-LC: m/z [M+H]⁺ calcd for $C_{27}H_{31}N_7O_{11}$: 630.2160. Found: 630.2280.

2'-Deoxy-N²-dimethylaminomethylene-N¹-(6-nitropiperonyloxymethylene)-guanosine (dG3). Compound dG2 (500 mg, 0.79 mmol) was dissolved in MeOH (5 mL) and to the solution was added $K_2CO_3$ (510 mg, 3.95 mmol). The solution was stirred for 3 h at room temperature after which it was filtered and evaporated. Purification by silica gel chromatography using $CHCl_3$:MeOH (85:15) with 2% TEA afforded 385 mg of dG3 as a yellow foam (92% yield). $^1$H NMR (CDCl₃): δ=1.44 (m, 3H), 2.48 (m, 1H), 2.66 (m, 1H), 3.03 (m, 3H), 3.19 (m, 3H), 3.92 (m, 2H), 4.13 (m, 1H), 4.82 (m, 1H), 5.37 (m, 1H), 5.69-5.94 (m, 4H), 6.32 (m, 1H), 7.06 (m, 1H), 7.26 (m, 1H), 8.15-8.28 (m, 2H). $^{13}$C NMR (CDCl₃): δ=24.1, 35.4, 40.8, 41.6, 62.2, 70.9, 71.1, 72.1, 74.5, 85.2, 88.5, 103.2, 104.6, 106.8, 120.0, 138.3, 139.1, 141.1, 146.8, 147.9, 152.3, 156.9, 158.2. HRMS-LC: m/z [M+H]⁺ calcd for $C_{23}H_{27}N_7O_9$: 546.1948. Found: 546.2047.

5'-O-DMT-2'-Deoxy-N²-dimethylaminomethylene-N¹-(6-nitropiperonyloxymethylene)-guanosine (dG4). To a solution of dG3 (200 mg, 0.37 mmol) and cat. DMAP in pyridine (3 mL), at 0° C., was added dimethoxytrityl chloride (150 mg, 0.44 mmol). The solution was allowed to stir for 8 h. The reaction was quenched with addition of 1 mL of MeOH and the solvent was subsequently evaporated. Purification by silica gel chromatography $CHCl_3$:MeOH (98:2) with 2% TEA afforded 240 mg of dG4 as a yellow foam (77% yield). $^1$H NMR (CDCl₃): δ=1.43 (m, 3H), 2.50 (br. s, 2H), 3.00 (m, 3H), 3.15 (m, 3H), 3.28-3.41 (m, 2H), 3.75 (s, 6H), 4.08 (m, 1H), 4.61 (br. s, 1H), 5.39 (m, 1H), 5.65-5.88 (m, 4H), 6.30 (m, 1H), 6.80 (m, 4H), 7.18-7.41 (m, 11H), 7.61 (m, 1H), 8.15-8.20 (m, 1H). $^{13}$C NMR (CDCl₃): δ=24.1, 35.4, 41.2, 41.6, 55.5, 64.5, 71.5, 72.8, 73.8, 82.8, 86.0, 86.7, 103.0, 104.5, 107.0, 113.4, 119.7, 127.2, 128.2, 128.3, 130.3, 135.6, 135.9, 139.4, 141.0, 144.8, 146.7, 148.1, 152.6, 157.1, 157.9, 158.0, 158.8. HRMS-LC: m/z [M+H]⁺ calcd for $C_{44}H_{45}N_7O_{11}$: 848.3255. Found: 848.3251.

5'-O-DMT-2'-Deoxy-N²-dimethylaminomethylene-N¹-(6-nitropiperonyl-oxymethylene)-guanosine-3'-[(2-cyanoethyl)-N,N-diisopropylaminophosphoramidite] (dG5). Compound dG4 (200 mg, 0.24 mmol) was dissolved in DCM (2 mL). To the solution was added DIEA (165 μL, 0.96 mmol), followed by 2-cyanoethyl-N,N-diisopropyl-chlorophosphoramidite (80 μL, 0.36 mmol) and the reaction was allowed to proceed for 2 h. The solvent was subsequently evaporated and the residue purified by silica gel chromatography using $CHCl_3$:hexanes (70:30) with 2% TEA. The chromatographed product was additionally purified by precipitation from DCM:pentane, affording 215 mg of dG5 as a yellow foam (82% yield). $^1$H NMR (CDCl₃): δ=1.05-1.23 (m, 12H), 1.42 (m, 3H), 2.42-2.62 (m, 4H), 2.98 (m, 3H), 3.17 (m, 3H), 3.26 (m, 2H), 3.51-3.83 (m, 10H), 4.21 (m, 1H), 4.61 (m, 1H), 5.39 (m, 1H), 5.63-5.91 (m, 4H), 6.22 (m, 1H), 6.78 (m, 4H), 7.15-7.41 (m, 11H), 7.62 (m, 1H), 8.25-8.40 (m, 1H). $^{13}$C NMR (CDCl₃): δ=20.5, 24.1, 24.8, 35.5, 40.5, 41.5, 43.4, 55.5, 58.6, 63.9, 71.4, 73.5, 74.5, 82.9, 85.6, 86.7, 103.1, 104.5, 107.0, 113.4, 117.8, 120.0, 127.2, 128.1, 128.3, 130.2, 135.5, 135.8, 139.4, 141.1, 144.7, 146.7, 148.1, 152.7, 157.0, 157.9, 158.1, 158.8. $^{31}$P NMR (CDCl$_3$): δ=148.8, 148.9, 149.0.

Example 3

Synthesis of Caged Guanosine Phosphoramidite G5

To extend light-regulation efforts to RNA building blocks, NPOM caged guanosine phosphoramidite G5 (Scheme 2B) was synthesized. The fully protected nucleoside G1 was reacted with NPOM chloride in 79% yield in the presence of DBU. Subsequent removal of the tBu$_2$Si group with HF-pyridine led to G3 (89% yield) and enabled the selective installation of a DMT group on the 5'-OH delivering G4 in 83% yield. The synthesis of G5 was completed by phosphorylation in 56% yield.

silica gel chromatography using hexanes:EtOAc gradient (70:30, 50:50) with 2% TEA afforded 108 mg of G2 as a yellow foam (79% yield). $^1$H NMR (CDCl$_3$): δ=0.11 (s, 6H), 0.90 (s, 9H), 1.05 (m, 18I), 1.46 (d, J=6.3 Hz, 3H), 3.04 (s, 3H), 3.17 (s, 3H), 3.95-4.09 (m, 3H), 4.47 (m, 2H), 5.40 (m, 1H), 5.63-5.98 (m, 5H), 7.18-7.31 (m, 2H), 7.51 (s, 1H), 8.32 9s, 1H). $^{13}$C NMR (CDCl$_3$): δ=−4.7, −4.1, 18.6, 20.6, 23.0, 24.1, 26.1, 27.2, 27.7, 35.4, 41.5, 68.1, 74.5, 75.5, 76.2, 76.6, 91.0, 91.6, 103.0, 104.5, 107.2, 120.4, 135.4, 136.1, 139.3, 141.2, 146.8, 147.6, 152.5, 157.1, 157.8. HRMS-LC: m/z [M+H]$^+$ calcd for C$_{37}$H$_{57}$N$_7$O$_{10}$Si$_2$: 816.3783. Found: 816.3774.

N$^2$-(dimethylaminomethylene)-2'-O-(tert-butyldimethylsilyl)-N$^1$-(6-nitropiperonyloxymethylene) guanosine (G3). Compound G2 (100 mg, 0.12 mmol) was dissolved in DCM (0.5 mL) and the solution was chilled to 0° C. in a plastic vessel. To the solution was then slowly added a solution of

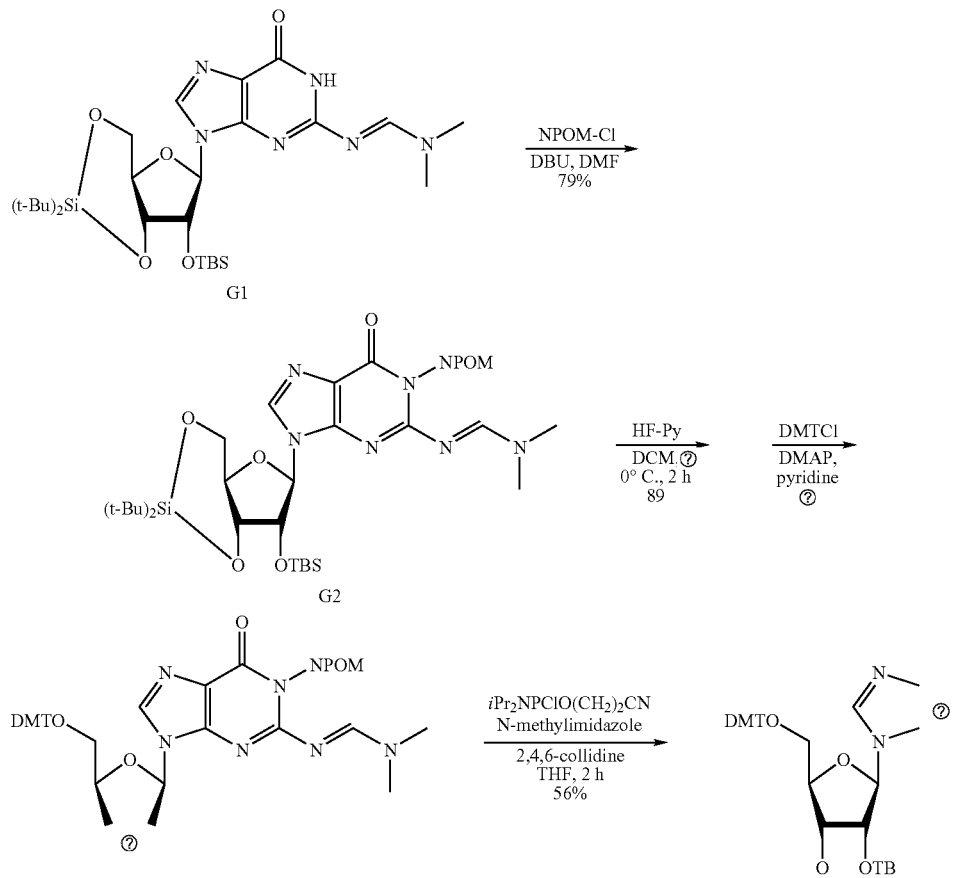

Scheme 2B. Synthesis of the NPOM caged guanosine phosphoramidite G5.

N$^2$-(dimethylaminomethylene)-2'-O-(tert-butyldimethylsilyl)-3',5'-O-(di-tert-butylsilanediyl)-N$^1$-nitropiperonyloxymethylene) guanosine (G1). To a solution of compound G1 (100 mg, 0.17 mmol), which was synthesized by method of Hyodo (M. Hyodo and Y. Hayakawa, *Bull. Chem. Soc. Jpn.*, 77, 2089-2093 (2004)) in DMF (1 mL) was added DBU (38 μL, 0.25 mmol), followed by drop-wise addition of 6-nitropiperonyloxymethylene chloride (64 mg, 0.25 mmol), dissolved in DMF (0.5 mL). After 8 h at room temperature, the reaction was taken up in EtOAc (10 mL) and washed with sat. NaHCO$_3$, water and brine. The organic layer was dried over Na$_2$SO$_4$, filtered, and the solvent evaporated. Purification by HF-pyridine (10 μL, 0.5 mmol) diluted with pyridine (60 μL), and the reaction was stirred for 2 h at 0° C. The reaction was subsequently quenched with saturated NaHCO$_3$ and diluted with DCM (5 mL). The organic layer was washed with water, dried over Na$_2$SO$_4$, filtered and evaporated. Purification by silica gel chromatography, using CHCl$_3$:MeOH (98:2) with 2% TEA, afforded 72 mg of G3 as a yellow foam (89% yield). $^1$H NMR (CDCl$_3$): δ=−0.28 (m, 3H), −0.16 (s, 1.5H), 0.12 (s, 1.5H), 0.77-0.90 (m, 9H), 1.39 (m, 3H), 2.95 (m, 3H), 3.13 (m, 3H), 3.62-4.10 (m, 3H), 4.18-4.77 (m, 4H), 5.30 (m, 1H), 5.58-5.88 (m, 5H), 7.05-7.22 (m, 2H), 7.70-8.20 (m, 2H). $^{13}$C NMR (CDCl$_3$): δ=−4.9, −4.4, 18.1, 24.0, 25.9, 35.2, 41.5, 62.3, 71.6, 74.3, 75.1, 76.2, 85.9, 90.0, 103.1, 104.6, 106.8, 120.7, 138.1, 138.9, 139.0, 141.1, 146.9, 147.7, 152.3, 157.6, 157.9. HRMS-LC: m/z [M+H]$^+$ calcd for $C_{29}H_{41}N_7O_{10}Si$: 676.2762. Found: 676.2758.

5'-O-DMT-N$^2$-(dimethylaminomethylene)-2'-O-(tert-butyldimethylsilyl)-N$^1$-(6-nitropiperonyloxymethylene) guanosine (G4). Compound G3 (100 mg, 0.15 mmol) and catalyst DMAP were dissolved in pyridine (1 mL) and chilled to 0° C. To the solution was then added dimethoxytrityl chloride (60 mg, 0.17 mmol) and the reaction was allowed to proceed for 8 h. The reaction was quenched with MeOH (1 mL) and the solvents were evaporated. Purification of the residue by silica gel chromatography, using CHCl$_3$:hexanes gradient (70:30, 80:20) with 2% TEA, afforded 120 mg of G4 as a yellow foam (83% yield). $^1$H NMR (CDCl$_3$): δ=−0.19-0.08 (m, 6H), 0.85 (m, 9H), 1.46 (m, 3H), 3.02-3.14 (m, 6H), 3.22-3.44 (m, 2H), 3.78 (m, 6H), 4.11-4.39 (m, 3H), 4.62 (m, 1H), 5.40 (m, 1H), 5.65-5.98 (m, 5H), 6.83 (m, 4H), 7.20-7.44 (m, 11H), 7.76 (m, 1H), 8.30-8.40 (m, 1H). $^{13}$C NMR (CDCl$_3$): δ=−4.8, −4.4, 18.1, 24.1, 25.8, 35.4, 41.4, 55.5, 63.1, 63.9, 71.9, 75.3, 76.5, 84.0, 86.9, 87.9, 103.1, 104.4, 104.8, 107.1, 113.5, 120.1, 127.3, 128.2, 130.3, 135.7, 139.5, 141.1, 144.7, 146.8, 148.5, 152.6, 157.3, 157.8, 157.9, 158.9. HRMS-LC: m/z [M+H]$^+$ calcd for $C_{50}H_{59}N_7O_{12}Si$: 978.4069. Found: 978.4064.

5'-O-DMT-N$^2$-(dimethylaminomethylene)-2'-O-(tert-butyldimethylsilyl)-N$^1$-(6-nitropiperonyloxymethylene) guanosine 3'-[(2-cyanoethyl)-N,N-diisopropylaminophosphoramidite] (G5). To a solution of G4 (100 mg, 0.1 mmol), 2,4,6-collidine (54 μL, 0.4 mmol), and N-methylimidazole (8 μL, 0.1 mmol) in TRF (1 mL) was added 2-cyanoethyl-N,N-diisopropyl-chlorophosphoramidite (45 μL, 0.2 mmol) at 0° C. The mixture was stirred at room temperature for 2 h and then diluted with EtOAc (10 mL). The resulting mixture was washed with saturated NaHCO$_3$, water and brine. The organic layer was dried over Na$_2$SO$_4$ and concentrated to give an oily residue. Purification by silica gel chromatography using hexanes:EtOAc (30:70) with 2% TEA afforded 67 mg of G5 as a yellow foam (56% yield). $^1$H NMR (CDCl$_3$): δ=−0.19-0.04 (m, 6H), 0.77-1.15 (m, 21H), 1.43 (m, 3H), 2.07-2.62 (m, 2H), 2.98-3.11 (m, 6H), 3.20-3.67 (m, 5H), 3.75 (s, 6H), 4.11-4.63 (m, 4H), 5.38 (m, 1H), 5.62-6.10 (m, 5H), 3.68 (m, 4H), 7.10-7.50 (m, 11H), 7.80 (m, 1H), 8.25-8.47 (m, 1H). $^{13}$C NMR (CDCl$_3$): δ=−4.8, −4.1, 18.1, 20.0, 24.1, 24.8, 25.9, 35.4, 41.4, 43.5, 55.5, 57.9, 63.5, 63.8, 72.2, 73.1, 76.5, 83.7, 84.7, 86.8, 103.1, 104.6, 104.8, 107.1, 113.5, 117.6, 120.1, 127.3, 128.2, 130.3, 135.7, 139.5, 141.1, 144.7, 146.9, 148.5, 152.6; 157.3, 157.8, 158.0, 158.8. $^{31}$P NMR (CDCl$_3$): δ=150.3, 150.5, 150.7, 151.3, 151.6, 151.7, 151.8.

Example 4

Synthesis and Application of Light-Triggered Morpholinos

This example investigated the ability to synthesize a photocaged morpholino monomer. The developed synthetic route commences with the methyluridine 17, which was selectively TIPS-protected at the 5'-OH (77% yield) and subsequently oxidatively opened to the dialdehyde 18 (100% yield). Treatment with an ammonium source under reducing conditions yielded the morpholino derivative 19. The yield of this notoriously difficult reaction could not be optimized beyond 50%. The secondary amine was then DMT protected, and the thymine NH was NPOM caged in 20 under conditions previously discovered (78% yield). Almost quantitative removal of the TIPS group delivered the caged but unactivated morpholino monomer 21 (Scheme 3).

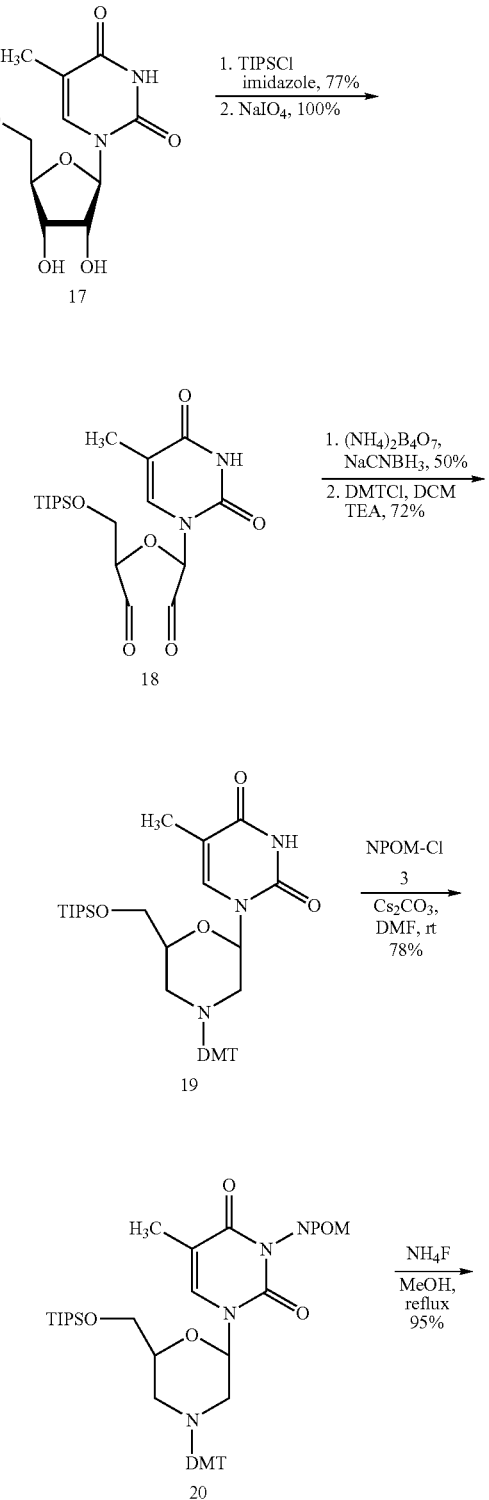

Scheme 3. Synthesis of the NPOM caged morpholino monomer 21.

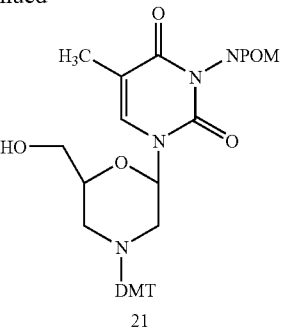

21

Figure 5:
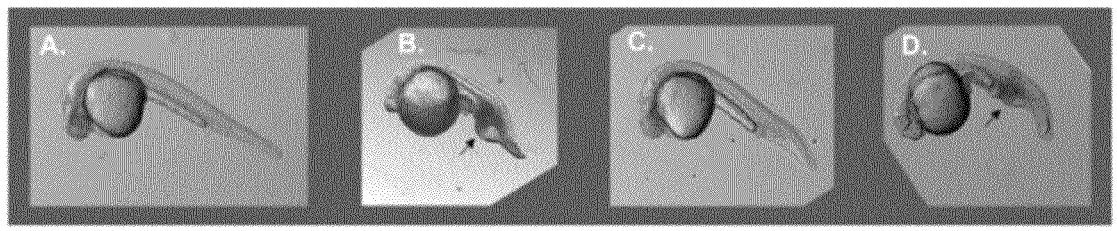
FIG. 5 shows light-regulation of morpholino activity in zebrafish embryos. Percentages represent the frequency of the pictured phenotype in live fish. A) Non-injected embryo (100%). B) Injection of the non-caged Chordin-0 MO (100%). C) Injection of the caged MO (Chordin-4) –UV irradiation (80%). D) Injection of the caged MO (Chordin-4) +UV irradiation for 60 sec at 365 nm (100%). Identical amounts were injected in each experiment. The expanded blood island (arrows) is indicative of the chordin phenotype.

Injections with the non-caged and caged morpholino oligomers containing four 21 monomers targeting chordin were conducted. Zebrafish embryos were injected into the yolk sac at the 1-4 cell stage with ~1 nl of 500 μm caged Chordin-4 morpholino (5' AT*CCACAGCAGCCCCT*CCAT*CAT*CC 3' [SEQ ID NO 2]; T* denotes the caged thymidine; containing 0.15% phenol red to verify injection). Immediately after injection, half of the injected embryos were exposed to 365 nm UV light for 60 sec. The other half was protected from light. Half of the uninjected control embryos were also exposed to 365 nm UV for 60 sec, and no phenotypic differences between ±UV were detected. All embryos were grown at 28° C. for about 28 hours before their phenotypes were photographed. The chordin gene induces dorsalization of the developing embryo and injection of an anti-chordin MO induces a phenotype resembling chordin null-mutant embryos by displaying abnormally shaped somites, an expanded blood island (see arrows in FIG. 5), an abnormal tail fin, and a reduced head (see FIG. 5B compared to the non-injected fish shown in FIG. 5A). In contrast, the caged morpholino Chordin-4 was completely inactive and displayed a wild-type phenotype (FIG. 5C). Light-irradiation (365 nm, 60 sec) of embryos injected with Chordin-4 completely restored the chordin phenotype (FIG. 5B). This data indicated the ability to regulate morpholino antisense activity through the site specific incorporation of caging groups followed by light irradiation.

Example 5

Photocaged Nucleosides and Nucleoside Analogs as Modular Building Blocks for the Proposed Light-Regulated Oligonucleotides In order to achieve a maximum flexibility in designing highly efficient light-activatable oligonucleotides, it is necessary to have access to all four caged monomeric building blocks. This is especially important in the development of light-activated gapmers, which have a small central stretch of DNA limiting the potential caging sites. Thus, there are synthetic routes to all caged deoxynucleotide phosphoroamidites as well as all caged morpholino monomers.

Caged nucleoside monomers. In order to achieve the synthesis of light-activated DNAzymes, phosphothiorate DNA, and gapmers, one complements the caged phosphoramidites of thymidine 11 and deoxyguanosine 16, by synthesizing the caged monomers of deoxyadenosine 27 (Scheme 4) and deoxycytidine 33 (Scheme 5).

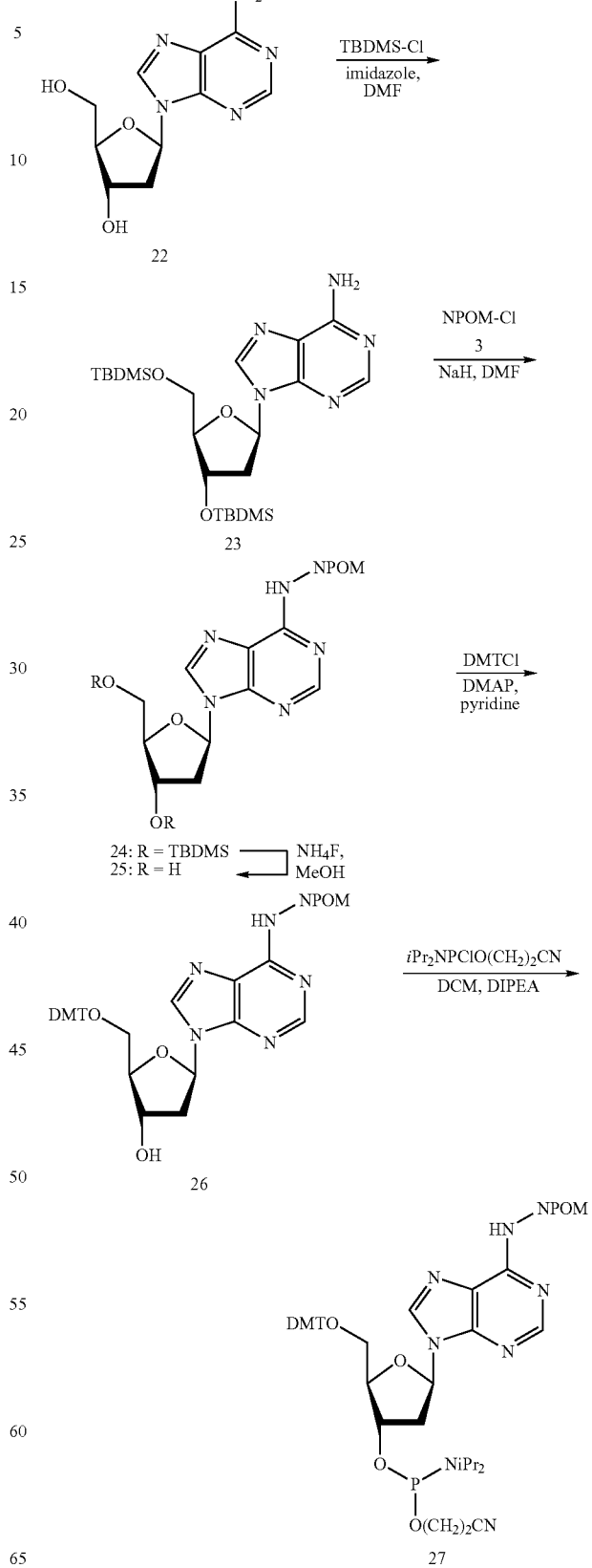

Scheme 4. Synthesis of the NPOM caged DNA monomer 27.

The synthesis of 27 commences with commercially available deoxyadenosine 22 which is silylated at both hydroxyl groups furnishing 23. The NPOM caging group is installed on N-6 using NaH as the base in DMF. Converting N-6 into a secondary amine (as in 24) has been shown to be sufficient as a protecting strategy for chemical DNA synthesis. The TBDMS groups is subsequently removed by treatment with $NH_4F$ and the 5'-OH in 25 is selectively blocked by DMT protection leading to 26. The synthesis of 27 is completed through phosphoramidite formation.

Scheme 5. Synthesis of the NPOM caged DNA monomer 33.

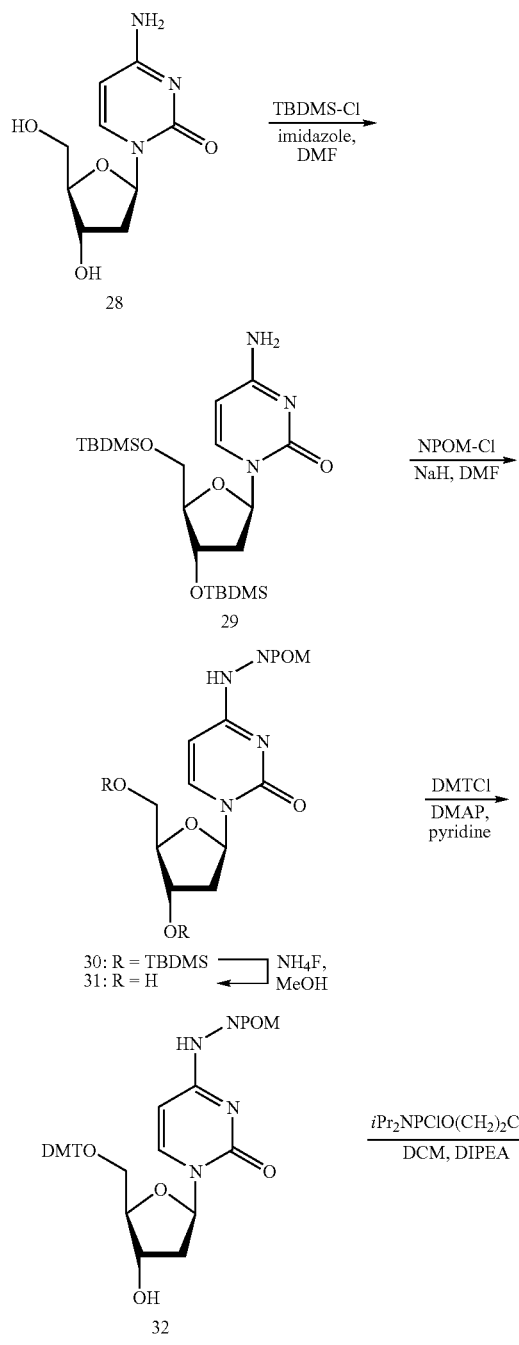

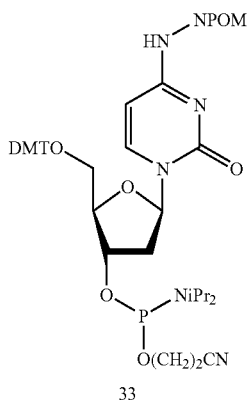

The synthesis of the caged phosphoramidite 33 of deoxycytidine follows the same route as the synthesis of 27, as shown in Scheme 5: TBDMS protection of 28, NPOM caging of 29, desilylation from 30 to 31, selective DMT protection to 32, followed by finial activation of the phosphoramidite.

Caged morpholino monomers. The synthesis of the caged guanosine morpholino monomer 38 (Scheme 6) is a combination of the caged deoxyguanosine 16 synthesis (and the caged thymidine morpholino 21. The synthesis commences with guanosine 34 which is first protected on the N-2 and the O-5', followed by oxidative cleavage of the bond between the 2' and the 3'-position. The dialdehyde 35 is then converted into the morpholino analog, which is subsequently DMT protected to 36. NPOM caging of N-1 to 37 and desilylation to 38 complete the synthesis.

Scheme 6. Synthesis of the NPOM caged morpholino monomer 38.

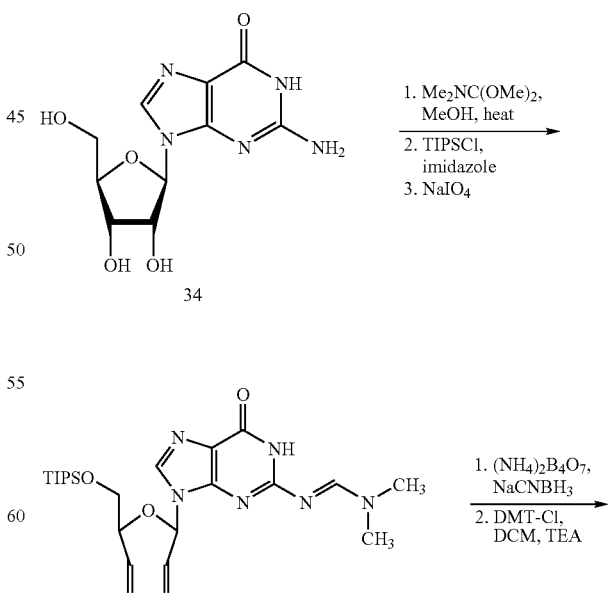

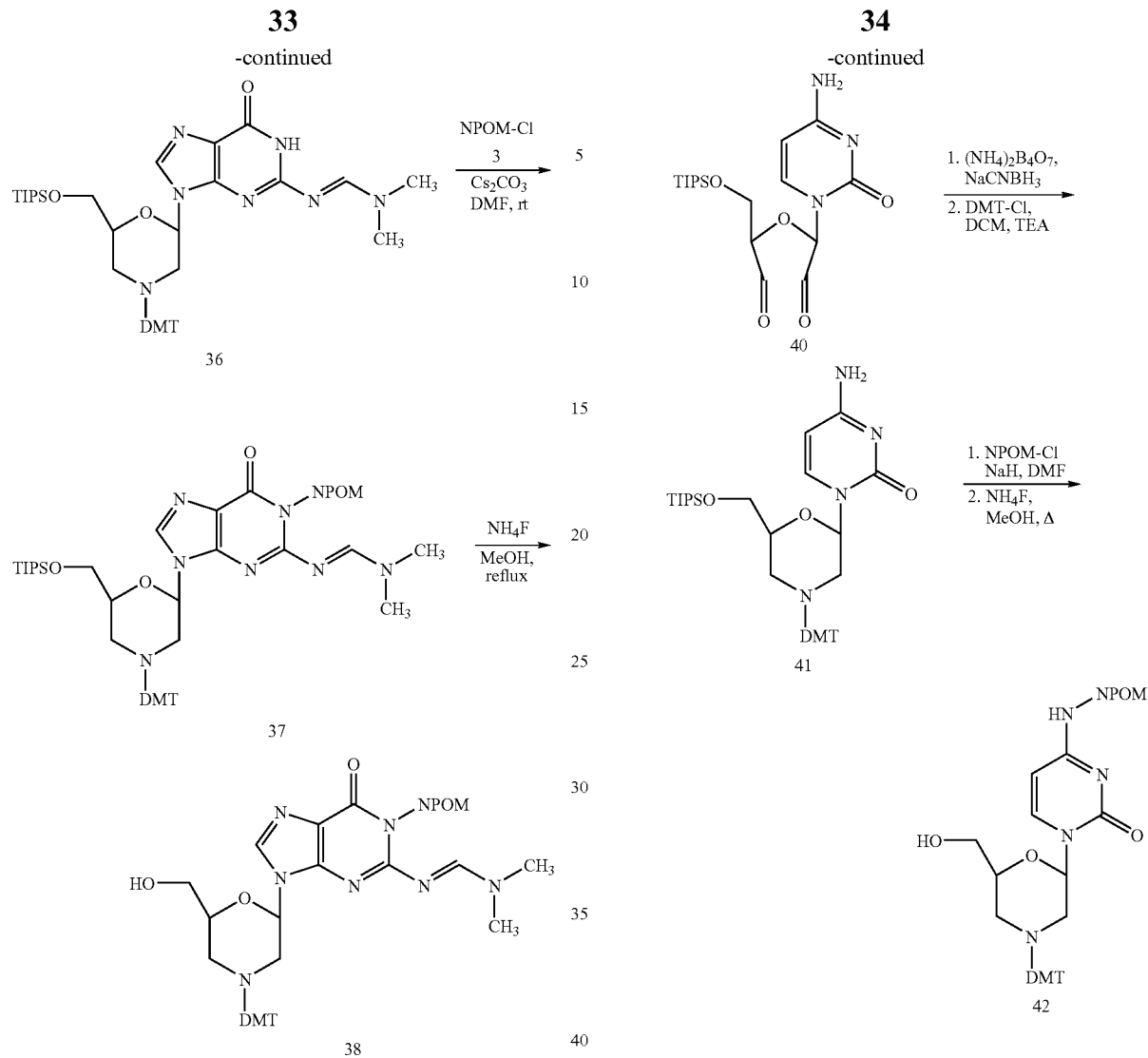

The synthetic route developed for the synthesis of 38 is employed in the synthesis of the caged morpholino monomers 42 (Scheme 7) and 46 (Scheme 8) derived from cytidine (29) and adenosine (43) respectively. In both syntheses, the starting material 39 or 43 is selectively protected and oxidized to 40 or 44, cyclized and tritylated to the morpholino 41 or 45, and finally caged and desilylated to the monomeric building block 42 or 46.

Scheme 7. Synthesis of the NPOM caged morpholino monomer 42.

Scheme 8. Synthesis of the NPOM caged morpholino monomer 46.

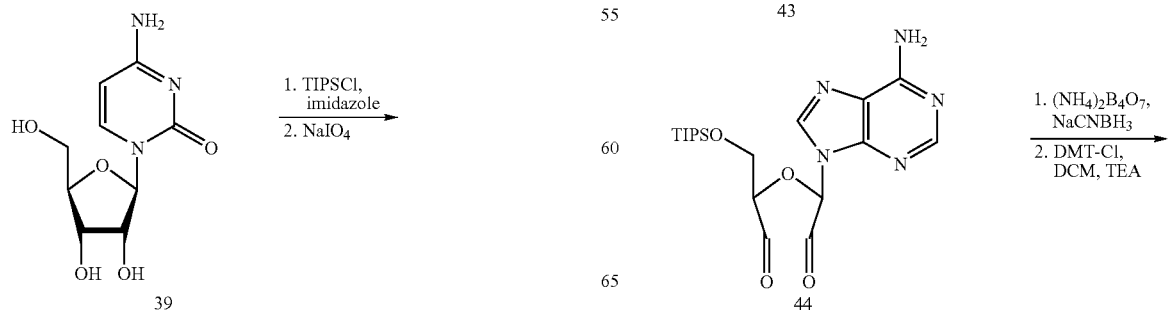

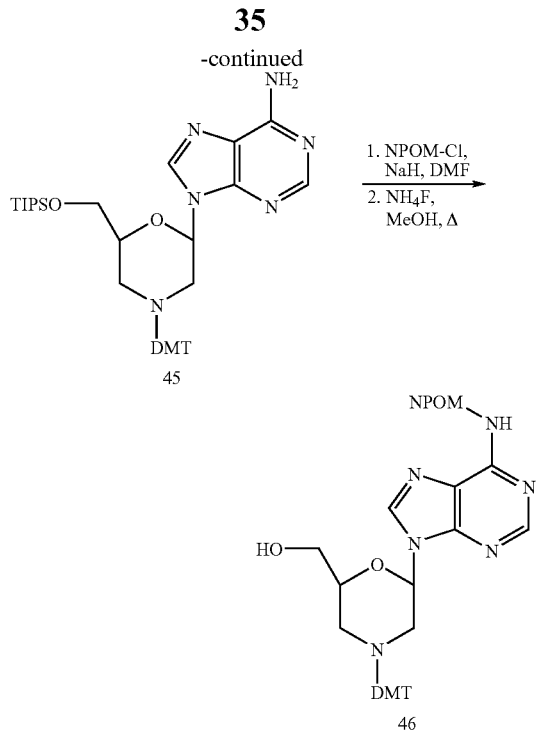

Example 6

Light-Triggered Polymerase Chain Reaction

To demonstrate the present disclosure in the photochemical regulation of PCR, we first investigated the effect of one or multiple caging groups on the pairing to a complementary DNA strand. The DNA oligomers P1-P7, consisting of 19 nucleotides, a typical length for PCR primers, and containing 0-4 caged thymidines have been synthesized (Table 1). These primers were than analyzed for their annealing and melting properties in the presence of a complementary oligonucleotide.

TABLE 1

Melting temperatures of non-caged (P1) and caged oligonucleotides (P2-P7) before and after UV irradiation (365 nm).

|    | DNA Sequence                    | Mp/° C. -UV    | Mp/° C. +UV    | SEQ ID NO |
|----|---------------------------------|----------------|----------------|-----------|
| P1 | 5' CTGATTTCGACCAGGTTCG 3'       | 65.3 ± 0.3     | 65.0 ± 0.8     | 3         |
| P2 | 5' CTGATTTCGACCAGGTTCG 3'   | 62.1 ± 0.7     | 64.1 ± 0.2     | 4         |
| P3 | 5' CTGATTTCGACCAGGTTCG 3'   | 54.3 ± 1.1     | 64.1 ± 0.8     | 5         |
| P4 | 5' CTGATTTCGACCAGGTTCG 3' | 55.5 ± 0.5   | 63.8 ± 0.3     | 6         |
| P5 | 5' CTGATTTCGACCAGGTTCG 3' | ND       | 64.2 ± 0.2     | 7         |
| P6 | 5' CTGATTTCGACCAGGTTCG 3'   | 50.0 ± 1.0     | 64.5 ± 0.5     | 8         |
| P7 | 5' CTGATTTCGACCAGGTTCG 3' | ND       | 64.2 ± 0.3     | 9         |

[a]T (bold underline font) denotes the caged thymidine.
[b]Melting temperatures (Mp) determined with the non-caged complement (5' CGAACCTGGTCGAAATCAG 3') [SEQ ID NO. 10].
ND = not detectable.

Melting curves were measured on a BioRad MyiQ RT-PCR thermocycler by conducting a sequence of 3 heating and cooling cycles (1 μM of both primer and complementary DNA with 12.5 μL iQ SYBR Green Supermix to a total volume of 25 μL; 40° C. to 80° C. with a 0.5° C./min ramp). The melting temperatures were determined to be 65.3° C. (P1), 62.1° C. (P2), 54.3° C. (P3), 55.5° C. (P4), and 50.0° C. (P6). No melting temperatures could be measured for P5 and P7, leading to the assumption that no hybridization occurs. These results indicate that both the number of caging groups and the position of the caged thymidine residues affected DNA hybridization. Installation of a single caging group resulted in a melting temperature depression of 3.2° C. and 11.0° C. as seen in P2 and P3, respectively. This effect was less pronounced in P2, perhaps due to the caged T's close proximity to the 5' terminus, which lead to a lower level of interference with the hybridization of neighboring nucleotides. With the incorporation of additional caging groups in P4-P7, melting temperatures decreased further. However, addition of a single caged thymidine close to the 5' terminus of P3 had no effect in P4. A positional effect was also observed with three caging groups, as seen in P5 and P6. The primer P6 contained a cluster of three caged thymidines and displayed a higher melting temperature than P5 containing three caging groups distributed throughout the DNA oligomer, which lead to a more effective disruption of hybridization. In order to ensure a complete removal of the photolabile group, each primer was irradiated for 8 minutes at 365 nm, and then analyzed in the same melting temperature assay. As expected, irradiation led to full restoration of DNA hybridization, as each primer displayed a comparable melting temperature to the non-caged analog P1.

Figure 6:
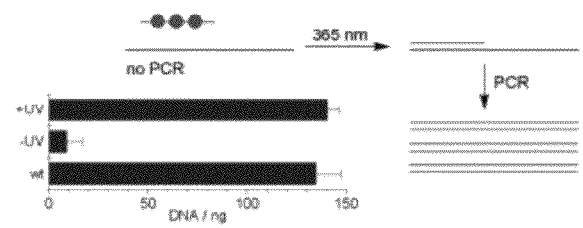
FIG. 6 shows PCR activation by light. Black line: PCR template, blue line: primer, red circles: caged thymidines.

These experiments revealed that the presence of three caging groups, distributed evenly throughout a 19 nucleotide oligomer, was sufficient to disrupt hybridization and prevented annealing of a PCR primer to its cognate DNA template, at the typical annealing temperature range of 50-65° C. The stability of the caging group to PCR conditions was examined on the monomeric caged thymidine, and found to be unaffected by the elevated temperatures required for PCR (data not shown). These results set the stage for the application of P5 in a light-activated PCR experiment (FIG. 6).

The DNA template (1.5 ng/μL of plasmid DNA) was incubated in the presence of P5 and a reverse primer (5'AGAGAGCTCGAGATCGCCATCTTCCAG-CAGGCGCACCATTGCCCCT-GT 3', [SEQ ID NO 11] 1 µM each; the same reverse primer was used in all PCRs) with nucleotide triphosphates (dNTPs, 0.3 mM each), in Taq Reaction Buffer (10 mM Tris-HCl, 50 mM. KCl, 1.5 mM $MgCl_2$, pH 8.3) and water. Taq DNA Polymerase (3 units/µL) was added to initiate the reaction. Prior to placement in a PCR thermocycler (Eppendor Mastercycler) the reaction was either irradiated for 8 minutes at 365 nm, or maintained in the dark. An initial denaturation at 95° C. was performed, followed by 40 cycles of 95° C. (30 sec), 50° C. (30 sec), and 72° C. (1 min), with a final extension at 72° C. (2 min). The reactions were conducted in triplicate, visualized on a 1% agarose gel, and quantitated (all DNA was quantified by band integration in ethidium bromide stained agarose gels using Image Quant 5.2). A regular PCR reaction with non-caged P1 produced approximately 140 ng of PCR product (data not shown); however when caged P5 was employed in the absence of UV irradiation, only trace amounts of product were detected (data not shown). After irradiation, the function of P5 was restored, leading to comparable amounts of PCR product as found in the reaction with P1 (data not shown). This experiment represented the first example of a light-activated PCR. While we initially employed irradiation prior to the thermal cycling, temporal control was also achieved by initiating the reaction through irradiation at a specific timepoint. Here, an identical reaction with UV irradiating at cycle 15 was conducted. Prior to irradiation, no PCR product can be detected in reactions conducted with the caged primer P5. In contrast, the non-caged primer P1 lead to the expected exponential amplification. Upon UV irradiation of the reaction with P5 at cycle 15 the amount of DNA increases exponentially, while no amplification occurred in the corresponding non-irradiated reaction.

Figure 7:
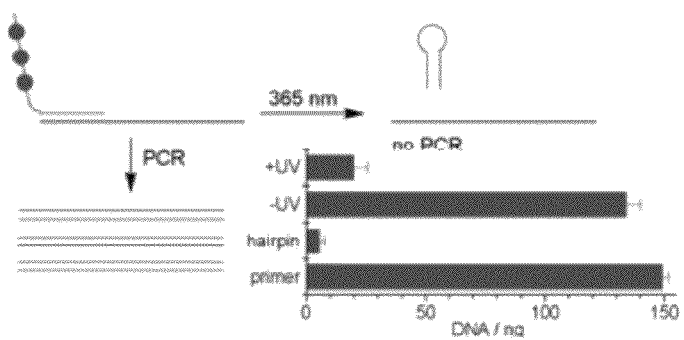
FIG. 7 shows PCR deactivation by light. Black line: PCR template, green line: primer, red circles: caged thymidines.

After achieving photochemical control of the activation of PCR at a specific time point, the possibility to switch-off PCR activity via light irradiation was examined. This was accomplished by designing a self-complementary primer which was predisposed to form a hairpin, rather than act as a PCR primer. By installing caging groups on the complementary portion of this sequence it was possible to block self-hybridization, which enabled the polymerization reaction. The PCR was then stopped by removing the photoactive groups, leading to hairpin formation and primer deactivation (FIG. 7). In order to achieve photochemical deactivation, an appropriate hairpin primer P8 was designed (5' GGTCAGTAAAT-TGTTTTTCAATTTACTGACCG 3') [SEQ ID NO. 12], and a photocaged analog P9 was synthesized (5' GGTCAGTAAA TTGTTTTTCAATTTACTGACCG 3') [SEQ ID NO. 13]. PCR using a typical primer which only possessed half of the hairpin and not its complement led to DNA amplification after 25 cycles (FIG. 7). Conversely, the non-caged hairpin primer P8 failed to amplify the DNA leading to very little PCR product (data not shown). However, in the absence of light irradiation the caged hairpin primer P9 was successful in acting as a primer, yielding 137 ng of PCR product (not shown). These data suggest that the 3 installed caging groups prevented hairpin formation, and allowed the complementary sequence to act as a PCR primer. If P9 was irradiated for 8 minutes at 365 nm, the caging groups were removed, leading to hairpin formation and suppression of DNA amplification (not shown).

Light-regulatory mechanisms were also employed in a temporally controlled fashion by irradiating the caged primer after 10 cycles of PCR. The non-caged primer P8 was used as a control, as it formed a hairpin immediately, blocking Taq DNA polymerase and inhibiting amplification. Because the caged primer P9 was able to bind to the DNA template, amplification occurred. At cycle 10 the reaction containing P9 was irradiated leading to removal of the caging groups, hairpin formation, and effective inhibition of DNA amplification. At the same point, amplification continued in the non-irradiated reaction with P9.

With the two caged primers P5 and P9 possessing opposing effects on the PCR reaction upon light irradiation, it was possible to utilize both primers simultaneously to stop the production of one PCR product, while also triggering the amplification of a different PCR product via irradiation with UV light. Thus, P5, P9, and the reverse primer were included in the PCR reaction mixture. A product band of ~1.0 kb was detected in the non-irradiated reaction after 20 cycles, which is attributed to the caged and inactive P5 and the caged but active P9 (not shown). Alternatively, a product band of ~0.6 kb was observed in the irradiated reaction, as a result of the decaging and activation of P5 and the deactivation of P9 (not shown). As expected, both bands were observed in the control reaction using non-caged and non-hairpin primers (not shown).

In summary, a photochemical activation and deactivation of the polymerase chain reaction has been developed. This was achieved through the incorporation of caged thymidine phosphoramidites into oligonucleotide primers using standard DNA synthesis protocols. By effectively disrupting DNA hybridization through the site-specific installation of caging groups and restoring it with light irradiation it was possible to control activation and deactivation of PCR in a temporal fashion. Moreover, by conducting a simultaneous activation and deactivation, light switching from one DNA amplification product to another was accomplished. Non-specific amplification of DNA was prevented by caged PCR primers.

Example 7

Photochemical Regulation of Phosphorothioate Antisense Agents in Mammalian Cell Culture While unmodified oligodeoxynucleotides display antisense activity, they are also subject to rapid degradation by nucleases and therefore have limited utility in the analysis of gene function. One of the most widely used nuclease-resistant chemistry available for antisense applications is the phosphorothioate modification (Woolf et al., *Nucleic Acids Res* 1990, 18, (7), 1763-9; and Kurreck, *Eur J Biochem* 2003, 270, (8), 1628-44). In phosphorothioates, a sulfur atom replaces a non-bridging oxygen in the oligo phosphate backbone. Phosphorothioate (PS) DNA has a half-life in vivo of ~9-10 h, compared to one hour for unmodified DNA. Other favorable characteristics are the formation of regular Watson-Crick base pairs, RNAse H activation, and easy cellular delivery do to the negatively charged backbone. However, PS oligonucleotides may cause cellular toxicity in certain cases due to their enhanced binding to proteins which interact with polyanionic species, e.g., heparin-binding proteins. Without being bound by theory, installation of bulky caging groups on the oligomer abrogates protein binding due to steric blocking, and that photochemical release of the PS DNA at a specific time point will minimize its toxic side effects. PS DNAs are currently being investigated in clinical trials and represent the only FDA approved antisense technology (Halperin et al., *Vaccine* 2006, 24, (1), 20-6; and Yu et al., *Antisense Nucleic Acid Drug Dev.* 2003, 13, (1), 57-66). However, no PS DNA oligomers are commercially available which enable spatio-temporal control of gene activity.

In order to develop light-activatable antisense agents, a non-caged phosphorothioate (PS) DNA targeting the *Renilla* luciferase reporter gene (Table 1) was synthesized (Xu et al., *Biochemical and Biophysical Research Communications* 2003, 306, (3), 712-717). Moreover, PS DNA antisense agents carrying 3 or 4 NPOM-caged thymidine residues where synthesized using standard DNA synthesis conditions in conjunction with Beaucage's reagent (Iyer et al., *Journal of the American Chemical Society* 1990, 112, (3), 1253-1254) for the introduction of the phosphorothioate backbone. Three and four caging groups, evenly distributed throughout the PS DNA 18-mer based on previous experiments of the PCR light-regulation were selected. Finally, a control PS DNA sequence was prepared which should not induce silencing of the *Renilla* luciferase reporter gene.

The capacity of the three and four caging groups to inhibit hybridization of the caged PS DNA oligomer to the complementary RNA sequence (5' UCCAGAACAAAGGAAACG 3') [SEQ ID NO 14] was examined. Hybridization was monitored on a BioRad MyiQ RT-PCR thermocycler by conducting a sequence of 3 heating and cooling cycles. No hybridization was detected in this temperature range for the control PS DNA or the non-irradiated caged PS DNA oligomers. The non-caged PS DNA/RNA hybrid exhibited a melting temperature of approximately 39° C., which is in agreement with similar PS DNAs (Kanaori et al., *Biochemistry* 1999, 38, (49), 16058-66). Complete hybridization was restored upon a 5-minute irradiation at 365 nm for both caged analogs (Table 2).

TABLE 2

Synthesized caged and non-caged phosphorothioate DNA oligomers. Melting temperature of PS DNA/RNA hybrids before and after irradiation (5 min, 365 nm, 23 W).

| PS DNA | DNA Sequence | Mp/° C. −UV | Mp/° C. +UV |
|---|---|---|---|
| 5. Control | 2. 5' TCCAGAACAAAGGAAACG 3' [SEQ ID NO. 15] | NA | NA |
| 7. Non-caged | 4. 5' CGTTTCCTTTGTTCTGGA 3' [SEQ ID NO. 16] | 39.5 ± 0.5 | 39.3 ± 0.8 |
| 3-Caged | 5' CGTTT*CCTTT*GTTCT*GGA 3' [SEQ ID NO. 17] | NA | 39.2 ± 0.6 |
| 4-Caged | 5' CGTT*TCCT*TTGT*TCT*GGA 3' [SEQ ID NO. 18] | NA | 38.9 ± 0.8 |

T* denotes the caged thymidine.
Melting temperatures (Mp) determined with the non-caged complement (5' UCCAGAACAAAG-GAAACG 3') [SEQ ID NO. 19].
NA: no melting temperature could be measured.

Figure 8:
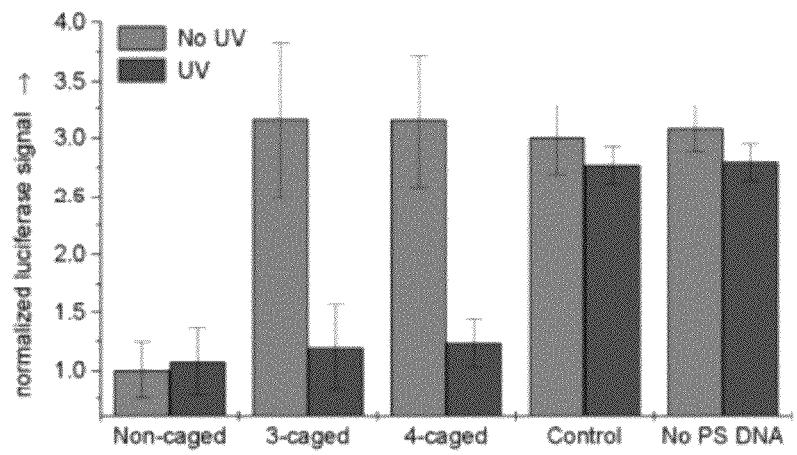
FIG. 8 shows *Renilla* luciferase signal in mammalian cells after PS DNA transfection±UV light irradiation (365 nm, 25 W hand-held UV lamp, 5 min), normalized to the transfection of the non-caged PS DNA antisense agent. The error bars represent the standard deviation of three independent experiments.

These antisense oligomers were transfected into mouse fibroblast cells (NIH 3T3) together with a dual reporter system encoding *Renilla* luciferase and firefly luciferase as a transfection control. The non-caged PS DNA induced a 70% down-regulation of the *Renilla* luciferase signal, and FIG. 8 displays all luciferase readouts normalized to that signal. The control PS DNA had no effect on the luciferase signal as observed by comparison to cells, which have not been transfected with PS DNA. Moreover, the UV irradiation (365 nm, 25 W hand-held UV lamp, 5 min) of 3T3 cells had no effect on the luciferase signal (within the error margin of the experiment) as was seen in case of transfection of the non-caged and the control PS DNA followed by irradiation. The installation of 3 caging groups completely inhibited the antisense activity of the PS DNA oligomer. Moreover, a brief irradiation with UV light quantitatively restored antisense activity to the level of the non-caged antisense agent. The same result was achieved with the PS DNA oligomer containing 4 caging groups (FIG. 8). This clearly demonstrated the ability to regulate gene silencing activity using light through the incorporation of caged monomeric building blocks into PS DNA antisense oligomers (Young, D. D.; Lusic, H.; Lively, M. O.; Yoder, J. A.; Deiters, A. *Chem Bio Chem* 2008, 9, DOI: 10.1002/cbic.200800627). The brief UV irradiations did not elicit any toxic effects on 3T3 cells as demonstrated by a cell viability assay.

Figure 9:
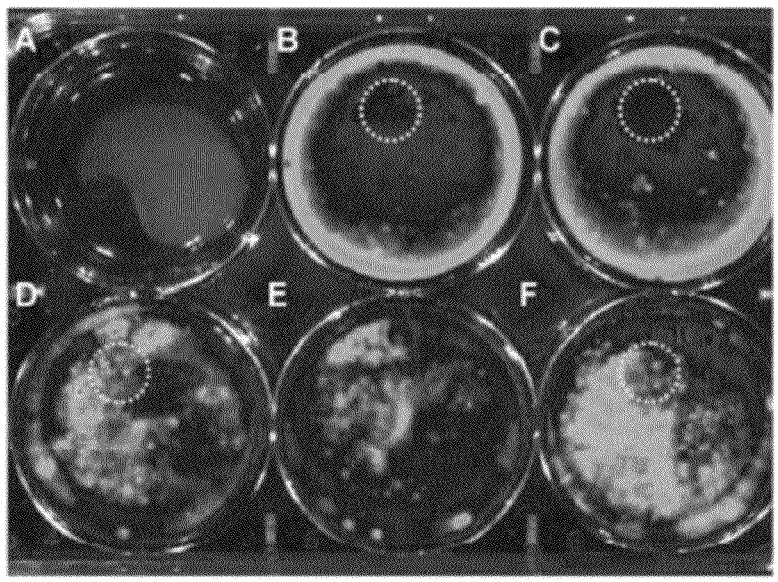
FIG. 9 shows spatial regulation of *Renilla* luciferase expression in mammalian cells using caged PS DNA antisense agents. The cellular monolayer was only irradiated inside the white dashed circle (365 nm, 5 min, 23 W). A) Negative control without luciferase plasmid. B) Transfection with luciferase plasmid and 3-caged PS DNA. C) Transfection with luciferase plasmid and 4-caged PS DNA. D) Positive control without PS DNA. E) Positive control without PS DNA and without irradiation. F) Transfection with luciferase plasmid and control PS DNA.

In order to demonstrate spatial regulation of gene expression using caged PS DNA antisense agents, cells were transfected with the *Renilla* luciferase plasmid and with or without PS DNA in a six-well format. After a four hour incubation, the media was removed and the cells were irradiated at 365 nm (5 min, 25 W) in a specific location using a mask. After a further 24 h incubation for luciferase expression to occur, the plate was imaged on a Xenogen Lumina system (FIG. 9). A high level of spatial control of antisense activity was achieved, as only irradiated areas of the cell monolayer transfected with caged PS DNA agents display little to no luciferase expression (Young, D. D.; Lusic, H.; Lively, M. O.; Yoder, J. A.; Deiters, A. *Chem Bio Chem* 2008, 9, DOI: 10.1002/cbic.200800627). In contrast, irradiation of wells containing no caged PS DNA displayed no luciferase silencing.

I claim:

1. A caged nucleotide and caged nucleotide analog comprising a caged purine or pyrimidine base selected from the group consisting of:

(Purines:)

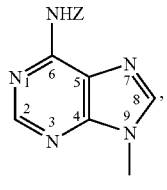 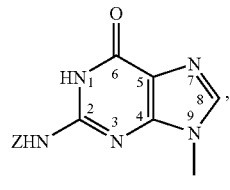

Adenine   Guanine (Pyrimidines:)

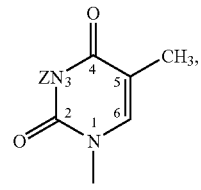 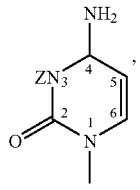

Thymine   Cytosine

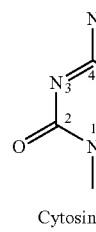 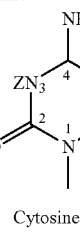 and 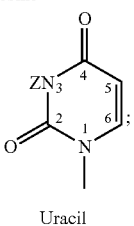;

Cytosine   Cytosine   Uracil wherein Z is a caging group of the formula:

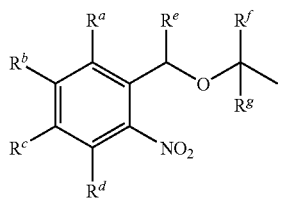

and wherein:
R$^a$, R$^b$, R$^c$ and R$^d$ are each independently selected from the group consisting of H, halo, C$_1$-C$_{20}$ alkyl, C$_1$-C$_{20}$ alkenyl, C$_1$-C$_{20}$ alkynyl, C$_1$-C$_{20}$ alkoxy, aryl, heteroaryl, keto, carboxy, amino, silyl, boron, and targeting groups; or an adjacent pair of R$^a$ and R$^b$, R$^b$ and R$^c$, or R$^c$ and R$^d$ together form a substituent of the formula —O(CH$_2$)$_n$O—, where n is from 1 to 3; and
R$^e$ is selected from the group consisting of H, C$_1$-C$_{20}$ alkyl, C$_1$-C$_{20}$ alkenyl, C$_1$-C$_{20}$ alkynyl, aryl, heteroaryl, keto, carboxy, and targeting groups;
R$^f$ and R$^g$ are each independently selected from the group consisting of consisting of H, C$_1$-C$_{20}$ alkyl, C$_1$-C$_{20}$ alkenyl, C$_1$-C$_{20}$ alkynyl, C$_1$-C$_{20}$ alkoxy, aryl, heteroaryl, keto, carboxy, amino, and targeting groups.

2. The caged nucleotide and caged nucleotide analog of claim 1 wherein at least one of R$^a$, R$^b$, R$^c$ and R$^d$ is C$_1$-C$_{20}$ alkoxy.

3. The caged nucleotide and caged nucleotide analog of claim 1 wherein an adjacent pair of R$^a$ and R$^b$, R$^b$ and R$^c$, or R$^c$ and R$^d$ together form a substituent of the formula —O(CH$_2$)$_n$O—, wherein n is an integer from 1 to 3.

4. The caged nucleotide and caged nucleotide analog of claim 1 wherein at least one of R$^a$, R$^b$, R$^c$ and R$^d$, R$^e$, R$^f$ and R$^g$ is a targeting group.

5. The caged nucleotide and caged nucleotide analog of claim 1 wherein the compound is a phosphoramidite.

6. An oligonucleotide or oligonucleotide analog compound containing a sequence of nucleotide or nucleotide analogs, wherein at least one of the nucleotides or nucleotide analogs is a caged nucleotide or nucleotide analog, selected from the group consisting of:

(Purines:)

 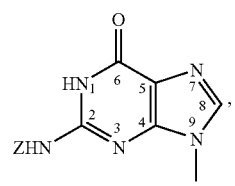

Adenine   Guanine (Pyrimidines:)

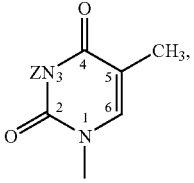 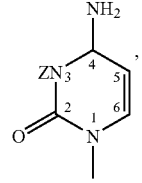

Thymine   Cytosine

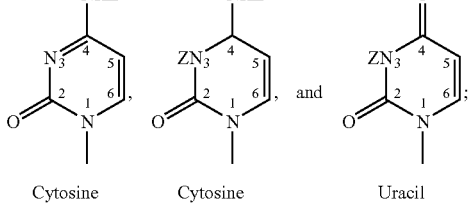, and 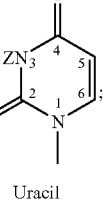;

Cytosine   Cytosine   Uracil wherein Z is a caging group of the formula:

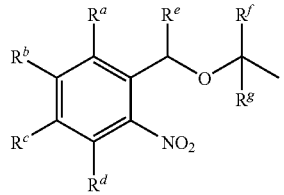

and wherein:
R$^a$, R$^b$, R$^c$ and R$^d$ are each independently selected from the group consisting of H, halo, C$_1$-C$_{20}$ alkyl, C$_1$-C$_{20}$ alkenyl, C$_1$-C$_{20}$ alkynyl, C$_1$-C$_{20}$ alkoxy, aryl, heteroaryl, keto, carboxy, amino, silyl, boron, and targeting groups; or an adjacent pair of R$^a$ and R$^b$, R$^b$ and R$^c$, or R$^c$ and R$^d$ together form a substituent of the formula —O(CH$_2$)$_n$O—, where n is from 1 to 3; and
R$^e$ is selected from the group consisting of H, C$_1$-C$_{20}$ alkyl, C$_1$-C$_{20}$ alkenyl, C$_1$-C$_{20}$ alkynyl, aryl, heteroaryl, keto, carboxy, and targeting groups;

$R^f$ and $R^g$ are each independently selected from the group consisting of consisting of H, $C_1$-$C_{20}$ alkyl, $C_1$-$C_{20}$ alkenyl, $C_1$-$C_{20}$ alkynyl, $C_1$-$C_{20}$ alkoxy, aryl, heteroaryl, keto, carboxy, amino, and targeting groups.

7. The oligonucleotide or oligonucleotide analog compound containing a sequence of nucleotide or nucleotide analogs, wherein at least one of the nucleotides or nucleotide analogs is a caged nucleotide or nucleotide analog of claim 6, wherein at least one of $R^a$, $R^b$, $R^c$ and $R^d$ is $C_1$-$C_{20}$ alkoxy.

8. The oligonucleotide or oligonucleotide analog compound containing a sequence of nucleotide or nucleotide analogs, wherein at least one of the nucleotides or nucleotide analogs is a caged nucleotide or nucleotide analog of claim 6, wherein an adjacent pair of $R^a$ and $R^b$, $R^b$ and $R^c$, or $R^c$ and $R^d$ together form a substituent of the formula —O(CH$_2$)$_n$O—, wherein n is an integer from 1 to 3.

9. The oligonucleotide or oligonucleotide analog compound containing a sequence of nucleotide or nucleotide analogs, wherein at least one of the nucleotides or nucleotide analogs is a caged nucleotide or nucleotide analog of claim 6, wherein at least one of $R^a$, $R^b$, $R^c$ and $R^d$, $R^e$, $R^f$ and $R^g$ is a targeting group.

10. The oligonucleotide or oligonucleotide analog compound containing a sequence of nucleotide or nucleotide analogs, wherein at least one of the nucleotides or nucleotide analogs is a caged nucleotide or nucleotide analog of claim 6, wherein the compound is a phosphoramidite.

11. A method for deprotecting or decaging an oligonucleotide or oligonucleotide analog, comprising the steps of:
 (a) providing an oligonucleotide or oligonucleotide analog comprising a plurality of nucleotides or nucleotide analogs, in vitro or in vivo in a cell, tissue, or subject, wherein at least one of the nucleotides or nucleotide analogs is a caged nucleotide or nucleotide analog selected from the group consisting of:

(Purines:)

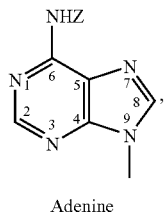 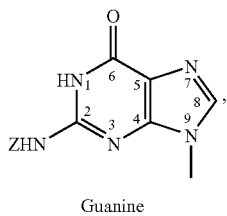

Adenine     Guanine (Pyrimidines:)

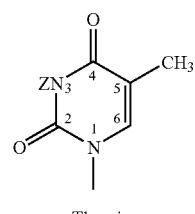 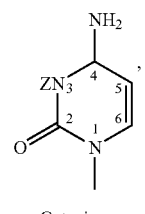

Thymine     Cytosine

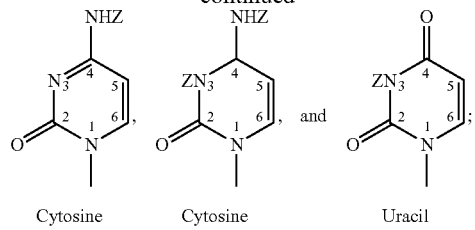

Cytosine     Cytosine     Uracil wherein Z is a caging group of the formula:

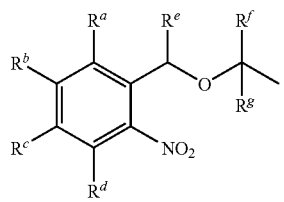

and wherein:
 $R^a$, $R^b$, $R^c$ and $R^d$ are each independently selected from the group consisting of H, halo, $C_1$-$C_{20}$ alkyl, $C_1$-$C_{20}$ alkenyl, $C_1$-$C_{20}$ alkynyl, $C_1$-$C_{20}$ alkoxy, aryl, heteroaryl, keto, carboxy, amino, silyl, boron, and targeting groups; or an adjacent pair of $R^a$ and $R^b$, $R^b$ and $R^c$, or $R^c$ and $R^d$ together form a substituent of the formula —O(CH$_2$)$_n$O—, where n is from 1 to 3; and
 $R^e$ is selected from the group consisting of H, $C_1$-$C_{20}$ alkyl, $C_1$-$C_{20}$ alkenyl, $C_1$-$C_{20}$ alkynyl, aryl, heteroaryl, keto, carboxy, and targeting groups;
 $R^f$ and $R^g$ are each independently selected from the group consisting of consisting of H, $C_1$-$C_{20}$ alkyl, $C_1$-$C_{20}$ alkenyl, $C_1$-$C_{20}$ alkynyl, $C_1$-$C_{20}$ alkoxy, aryl, heteroaryl, keto, carboxy, amino, and targeting groups; and
 (b) exposing the oligonucleotide or oligonucleotide analog to light, whereby the caging group Z is cleaved from the base to thereby providing a deprotected or decaged oligonucleotide or oligonucleotide analog.

12. The method for deprotecting or decaging an oligonucleotide or oligonucleotide analog of claim 11, wherein at least one of $R^a$, $R^b$, $R^c$ and $R^d$ is $C_1$-$C_{20}$ alkoxy.

13. The method for deprotecting or decaging an oligonucleotide or oligonucleotide analog of claim 11, wherein an adjacent pair of $R^a$ and $R^b$, $R^b$ and $R^c$, or $R^c$ and $R^d$ together form a substituent of the formula —O(CH$_2$)$_n$O—, wherein n is an integer from 1 to 3.

14. The method for deprotecting or decaging an oligonucleotide or oligonucleotide analog of claim 11, wherein at least one of $R^a$, $R^b$, $R^c$ and $R^d$, $R^e$, $R^f$ and $R^g$ is a targeting group.

15. The method for deprotecting or decaging an oligonucleotide or oligonucleotide analog of claim 11, wherein the compound is a phosphoramidite.

* * * * *

SEQUENCE LISTING

<160> NUMBER OF SEQ ID NOS: 19

<210> SEQ ID NO 1
<211> LENGTH: 15
<212> TYPE: RNA
<213> ORGANISM: Artificial Sequence
<220> FEATURE:
<223> OTHER INFORMATION: zebra fish

<400> SEQUENCE: 1
ggagagaugg gugcg                                                        15

<210> SEQ ID NO 2
<211> LENGTH: 25
<212> TYPE: DNA
<213> ORGANISM: Artificial Sequence
<220> FEATURE:
<223> OTHER INFORMATION: zebra fish, t is caged

<400> SEQUENCE: 2
atccacagca gccctccat catcc                                              25

<210> SEQ ID NO 3
<211> LENGTH: 19
<212> TYPE: DNA
<213> ORGANISM: Artificial Sequence
<220> FEATURE:
<223> OTHER INFORMATION: zebra fish

<400> SEQUENCE: 3
ctgatttcga ccaggttcg                                                    19

<210> SEQ ID NO 4
<211> LENGTH: 19
<212> TYPE: DNA
<213> ORGANISM: Artificial Sequence
<220> FEATURE:
<223> OTHER INFORMATION: zebra fish, first t is caged

<400> SEQUENCE: 4
ctgatttcga ccaggttcg                                                    19

<210> SEQ ID NO 5
<211> LENGTH: 19
<212> TYPE: DNA
<213> ORGANISM: Artificial Sequence
<220> FEATURE:
<223> OTHER INFORMATION: zebra fish, fourth t is caged

<400> SEQUENCE: 5
ctgatttcga ccaggttcg                                                    19

<210> SEQ ID NO 6
<211> LENGTH: 19
<212> TYPE: DNA
<213> ORGANISM: Artificial Sequence
<220> FEATURE:
<223> OTHER INFORMATION: zebra fish, first and fourth t's are caged

<400> SEQUENCE: 6
ctgatttcga ccaggttcg                                                    19

<210> SEQ ID NO 7
<211> LENGTH: 19
<212> TYPE: DNA

```
<213> ORGANISM: Artificial Sequence
<220> FEATURE:
<223> OTHER INFORMATION: zebra fish, first, fourth and sixth t's are
      caged

<400> SEQUENCE: 7
ctgatttcga ccaggttcg                                              19

<210> SEQ ID NO 8
<211> LENGTH: 19
<212> TYPE: DNA
<213> ORGANISM: Artificial Sequence
<220> FEATURE:
<223> OTHER INFORMATION: zebra fish, second, third and fourth t's are
      caged

<400> SEQUENCE: 8
ctgatttcga ccaggttcg                                              19

<210> SEQ ID NO 9
<211> LENGTH: 19
<212> TYPE: DNA
<213> ORGANISM: Artificial Sequence
<220> FEATURE:
<223> OTHER INFORMATION: zebra fish, first, second, fourth and sixth
      t's are caged

<400> SEQUENCE: 9
ctgatttcga ccaggttcg                                              19

<210> SEQ ID NO 10
<211> LENGTH: 18
<212> TYPE: DNA
<213> ORGANISM: Artificial Sequence
<220> FEATURE:
<223> OTHER INFORMATION: zebra fish

<400> SEQUENCE: 10
cgaacctggt cgaatcag                                               18

<210> SEQ ID NO 11
<211> LENGTH: 46
<212> TYPE: DNA
<213> ORGANISM: Artificial Sequence
<220> FEATURE:
<223> OTHER INFORMATION: zebra fish

<400> SEQUENCE: 11
agagagcycg agatcgccat cttccagcag  gcgcaccatt gcccct               46

<210> SEQ ID NO 12
<211> LENGTH: 32
<212> TYPE: DNA
<213> ORGANISM: Artificial Sequence
<220> FEATURE:
<223> OTHER INFORMATION: zebra fish

<400> SEQUENCE: 12
ggtcagtaaa ttgtttttca atttactgac cg                               32

<210> SEQ ID NO 13
<211> LENGTH: 32
<212> TYPE: DNA
<213> ORGANISM: Artificial Sequence
<220> FEATURE:
<223> OTHER INFORMATION: zebra fish, first, second and third t's are
      caged
```

```
<400> SEQUENCE: 13
cgtcagtaaa ttgtttttca atttactgac cg                    32

<210> SEQ ID NO 14
<211> LENGTH: 18
<212> TYPE: RNA
<213> ORGANISM: Artificial Sequence
<220> FEATURE:
<223> OTHER INFORMATION: zebra fish

<400> SEQUENCE: 14
uccagaacaa aggaaacg                                    18

<210> SEQ ID NO 15
<211> LENGTH: 18
<212> TYPE: DNA
<213> ORGANISM: Artificial Sequence
<220> FEATURE:
<223> OTHER INFORMATION: zebra fish

<400> SEQUENCE: 15
tccagaacaa aggaaacg                                    18

<210> SEQ ID NO 16
<211> LENGTH: 18
<212> TYPE: DNA
<213> ORGANISM: Artificial Sequence
<220> FEATURE:
<223> OTHER INFORMATION: zebra fish

<400> SEQUENCE: 16
cgtttccttt gttctgaa                                    18

<210> SEQ ID NO 17
<211> LENGTH: 18
<212> TYPE: DNA
<213> ORGANISM: Artificial Sequence
<220> FEATURE:
<223> OTHER INFORMATION: zebra fish, third, sixth and ninth t's are
      caged

<400> SEQUENCE: 17
cgtttccttt gttctgga                                    18

<210> SEQ ID NO 18
<211> LENGTH: 18
<212> TYPE: DNA
<213> ORGANISM: Artificial Sequence
<220> FEATURE:
<223> OTHER INFORMATION: zebra fish, second, fourth, seventh and ninth
      t's are caged

<400> SEQUENCE: 18
cgtttccttt gttctgga                                    18

<210> SEQ ID NO 19
<211> LENGTH: 18
<212> TYPE: RNA
<213> ORGANISM: Artificial Sequence
<220> FEATURE:
<223> OTHER INFORMATION: zebra fish

<400> SEQUENCE: 19
uccagaacaa aggaaacg                                    18
```